United States Patent
Kubo et al.

(10) Patent No.: US 9,505,723 B2
(45) Date of Patent: Nov. 29, 2016

(54) COMPOUND, DISPERSANT AND TONER

(71) Applicants: CANON KABUSHIKI KAISHA, Tokyo (JP); CANON FINETECH INC., Misato-shi, Saitama (JP)

(72) Inventors: Haruko Kubo, Susono (JP); Suzuka Ueno, Fukui (JP); Junko Chizuwa, Fukui (JP); Tomoya Yamamoto, Awara (JP); Hitoshi Itabashi, Yokohama (JP); Yuhei Terui, Numazu (JP); Yu Yoshida, Mishima (JP); Yasuaki Murai, Kawasaki (JP); Takayuki Toyoda, Yokohama (JP)

(73) Assignees: CANON KABUSHIKI KAISHA, Tokyo (JP); CANON FINETECH INC., Misato (JP)

( * ) Notice: Subject to any disclaimer, the term of this patent is extended or adjusted under 35 U.S.C. 154(b) by 0 days.

(21) Appl. No.: 14/988,272

(22) Filed: Jan. 5, 2016

(65) Prior Publication Data

US 2016/0130233 A1    May 12, 2016

Related U.S. Application Data

(63) Continuation of application No. PCT/JP2015/004438, filed on Sep. 1, 2015.

(30) Foreign Application Priority Data

Sep. 1, 2014  (JP) ................. 2014-176818

(51) Int. Cl.
| | | |
|---|---|---|
| *G03G 9/087* | (2006.01) |
| *C07D 235/26* | (2006.01) |
| *C07C 275/40* | (2006.01) |
| *C08F 20/36* | (2006.01) |
| *G03G 9/08* | (2006.01) |
| *C08F 212/06* | (2006.01) |
| *C08F 212/08* | (2006.01) |
| *C08F 220/14* | (2006.01) |
| *C08F 220/18* | (2006.01) |
| *C07C 233/18* | (2006.01) |

(52) U.S. Cl.
CPC ........... *C07D 235/26* (2013.01); *C07C 233/18* (2013.01); *C07C 275/40* (2013.01); *C08F 20/36* (2013.01); *C08F 212/06* (2013.01); *C08F 212/08* (2013.01); *C08F 220/14* (2013.01); *C08F 220/18* (2013.01); *G03G 9/08* (2013.01)

(58) Field of Classification Search
CPC .. C07D 235/62; C08F 212/06; C08F 220/18; C08F 220/14; G03G 9/08
See application file for complete search history.

(56) References Cited

U.S. PATENT DOCUMENTS

| | | | |
|---|---|---|---|
| 5,827,863 A | 10/1998 | Almansa et al. |
| 7,582,152 B2 | 9/2009 | Jaunky et al. |
| 8,541,401 B2 | 9/2013 | Mishra et al. |
| 8,628,899 B2 | 1/2014 | Kawamura et al. |
| 8,759,441 B2 | 6/2014 | Loccufier et al. |
| 8,815,485 B2 | 8/2014 | Tanaka et al. |
| 8,962,726 B2 | 2/2015 | Tanaka et al. |
| 9,097,999 B2 | 8/2015 | Murai et al. |
| 2013/0336901 A1 | 12/2013 | Mishra et al. |
| 2015/0004538 A1 | 1/2015 | Kawamura et al. |
| 2015/0274853 A1 | 10/2015 | Nishiura et al. |
| 2015/0277254 A1 | 10/2015 | Mukumoto et al. |

FOREIGN PATENT DOCUMENTS

| | | | | |
|---|---|---|---|---|
| JP | 4-184340 A | 7/1992 |
| JP | 6-075346 A | 3/1994 |
| JP | 9-050100 A | 2/1997 |
| JP | 9-504804 A | 5/1997 |
| JP | 10-316643 A | 12/1998 |
| JP | 2003-081948 A | 3/2003 |
| JP | 2003-238837 A | 8/2003 |
| JP | 2006-317895 | * | 11/2006 | ............... G03G 9/09 |
| JP | 3984840 B2 | 10/2007 |
| JP | 2009-501253 A | 1/2009 |
| JP | 2010-534071 A | 11/2010 |
| WO | 96/04273 A1 | 2/1996 |
| WO | 2006/024885 A1 | 3/2006 |
| WO | 2007/006639 A2 | 1/2007 |
| WO | 2009/013632 A2 | 1/2009 |

OTHER PUBLICATIONS

Translation of JP 2006-317895.*
Ahmad Basheer et al., "Enols of Amides Activated by the 2,2,2-Trichloroethoxycarbonyl Group," 69(4) J. Org. Chem. 1151-1160 (2004).

(Continued)

*Primary Examiner* — Peter Vajda
(74) *Attorney, Agent, or Firm* — Fitzpatrick, Cella, Harper & Scinto

(57) ABSTRACT

The present invention provides a dispersant excellent in the solubility to a solvent, the adsorption power to a coloring material, and the coloring material dispersibility, and reduced in the self-coloring property, a compound and a polymerizable compound for preparing the dispersant, and a toner using the dispersant.
The dispersant has a structure in which a structure represented by the following specific formula (3) or a tautomer thereof is bonded with a polymer, and the toner contains the dispersant.

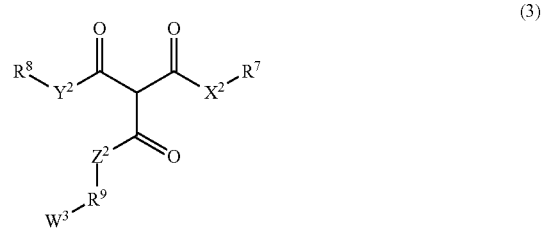

(3)

10 Claims, No Drawings

(56) References Cited

OTHER PUBLICATIONS

Reinhard Richter et al., "Concerning the Reactions of 2-Alkyl-Δ2-Oxazolines and 2-Methyl-Δ2-Thiazoline with Aryl Isocyanates," 743 Justus Liebigs Annalen der Chemie 10-24 (1971).

Norbert Moszner et al., "Reaction Behavior of Monomeric β-Ketoesters. 3. Polymerizable Reaction Products of 2-Acetoacetoxyethyl Methacrylate with Aromatic Isocyanates and Aldehydes," 33(1) Polymer Bull. 43-49 (1994).

International Search Report in International Application No. PCT/JP2015/004438 (mailed Nov. 24, 2015).

\* cited by examiner

COMPOUND, DISPERSANT AND TONER

CROSS-REFERENCE TO RELATED APPLICATIONS

This application is a continuation of International Application No. PCT/JP2015/004438, filed Sep. 1, 2015, which claims the benefit of Japanese Patent Application No. 2014-176818, filed Sep. 1, 2014.

BACKGROUND OF THE INVENTION

Field of the Invention

The present invention relates to a dispersant suitable for dispersion of various insoluble coloring materials (hereinafter, also referred to simply as "coloring material") such as pigments and oil-soluble dyes, a compound constituting the dispersant, and further a toner using the dispersant.

Description of the Related Art

Conventionally, coloring materials are dispersed in media such as solvents and resins (hereinafter, also referred to simply as "medium"), and are used as inks, coating materials and toners. In such applications, since it is needed that a coloring material is dispersed homogeneously in a medium, a dispersant such as a dispersant or a surfactant is generally concurrently used. Usual dispersants for coloring materials are constituted of an "adsorption site" having adsorbability to the coloring materials and a "dispersion site" having affinity for media. Since the each site can be designed so as to be adapted to the coloring materials and the media, various dispersants have been developed and reported so far.

As means to enhance adsorbability to coloring materials, dispersants whose adsorption sites have structures analogous to the coloring materials are proposed. Japanese Patent Application Laid-Open No. 2003-081948 proposes a low molecular compound containing a benzimidazolinone skeleton, which is purported to be improved in the adsorption power to a coloring material by introducing the same structure as that of the coloring material to the adsorption site. Further Japanese Patent Application Laid-Open No. 2003-238837 proposes a polymeric compound obtained by polymerizing a monomer containing a benzimidazolinone skeleton. Further Japanese Patent Application Laid-Open No. 2009-501253 proposes a polymer grafted with a site concurrently intramolecularly having a benzimidazolinone skeleton and an azo group. Further U.S. Pat. No. 7,582,152 discloses, as a dispersant for a coloring material for inkjet recording, an example of a polymer dispersant in which a chromophore whose molecular weight is lower than 95% of that of an azo pigment is bonded to a water-soluble polymer main chain. Further Japanese Patent No. 3984840 discloses a polymer pigment dispersant in which an azo or disazo chromophore containing a substitution product of acetoacetoanilides is bonded to a polymer.

SUMMARY OF THE INVENTION

The low molecular compound having a benzimidazolinone skeleton described in Japanese Patent Application Laid-Open No. 2003-081948 is low in solubility to a solvent since being rigid, and is unlikely to exhibit the dispersion effect. By contrast, the compound proposed in Japanese Patent Application Laid-Open No. 2003-238837 is comparatively good in solubility to a solvent, since being a polymer. However, since the compound has, other than the benzimidazolinone skeleton, few sites (sites of, for example, an ether structure, ester structure, amide structure, amine structure, urethane structure or urea structure, which is capable of forming hydrogen bonds with hydrophilic groups of the coloring material) exhibiting the adsorbability to the coloring material, the adsorption power to the coloring material is comparatively weak. The pigment dispersants proposed in Japanese Patent Application Laid-Open No. 2009-501253, U.S. Pat. No. 7,582,152, and Japanese Patent No. 3984840 are comparatively good in the solubility of the polymers to solvents. However, since the idea is to enhance the adsorption power by incorporating a chromophore such as an azo group to the adsorption site, the dispersant itself is colored. Hence, applications to coloring materials having dissimilar structures are difficult in some cases due to the problem of the tint variation.

Therefore, the present invention is directed to providing a dispersant excellent in the solubility to a solvent, the adsorption power to a coloring material and the coloring material dispersibility, and reduced in the self-coloring property.

Further, the present invention is directed to providing a compound for preparing the dispersant.

Further, the present invention is directed to providing a toner having a broad selective range of applicable coloring materials and having a high coloring power.

As a result of exhaustive studies to solve the above-mentioned problem, the present inventors have found that by incorporating a specific structure to an adsorption site of a dispersant having the adsorption site and a dispersion site, the above problem can be solved; and this finding has led to the completion of the present invention.

According to one aspect of the present invention, there is provided a compound represented by the following formula (1) or a tautomer thereof.

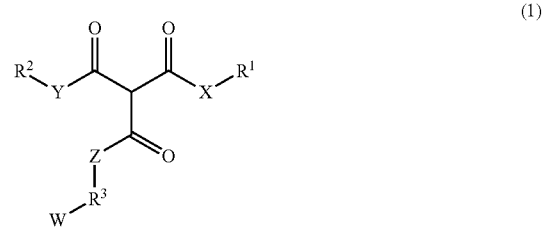

(1)

wherein X, Y and Z are each independently —O—, a methylene group or —NR$^4$—;

R$^4$ represents hydrogen or a straight-chain or branched-chain alkyl group having 1 to 4 carbon atoms;

R$^1$ represents an unsubstituted or substituted phenyl group, a polycyclic aromatic group, or a heterocyclic group;

R$^2$ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond or an amide bond;

R$^3$ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond or an amide bond;

W represents a reactive group or a polymerizable functional group capable of being incorporated in a polymer moiety; a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group or a ureido group;
the polycyclic aromatic group is a group derived from naphthalene, anthracene, phenanthrene or anthraquinone by removing one hydrogen atom therefrom; and
the heterocyclic group is a group derived from imidazole, oxazole, thiazole, pyridine, indole, benzimidazole, benzimidazolinone or phthalimide by removing one hydrogen atom therefrom.

According to another aspect of the present invention, there is provided a dispersant having a structure in which a structure represented by the following formula (3) or a tautomer thereof is bonded with a polymer moiety.

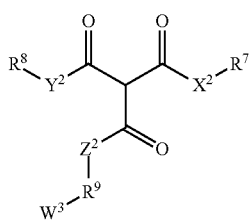

(3)

wherein $X^2$, $Y^2$ and $Z^2$ are each independently —O—, a methylene group or —$NR^{10}$—;
$R^{10}$ represents hydrogen or a straight-chain or branched-chain alkyl group having 1 to 4 carbon atoms;
$R^7$ represents an unsubstituted or substituted phenyl group, a polycyclic aromatic group, or a heterocyclic group;
$R^8$ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond or an amide bond;
$R^9$ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond or an amide bond;
$W^3$ represents a linking moiety to the polymer moiety;
a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group or a ureido group;
the polycyclic aromatic group is a group derived from naphthalene, anthracene, phenanthrene or anthraquinone by removing one hydrogen atom therefrom; and
the heterocyclic group is a group derived from imidazole, oxazole, thiazole, pyridine, indole, benzimidazole, benzimidazolinone or phthalimide by removing one hydrogen atom therefrom.

According to further aspect of the present invention, there is provided a toner having a toner particle containing a binding resin, a coloring material and a dispersant, wherein the dispersant is the above dispersant.

The present invention can provide a dispersant excellent in the solubility to a solvent, the adsorption power to a coloring material and the coloring material dispersibility, and reduced in the self-coloring property. The present invention can further provide a compound from which a dispersant having the above properties can be prepared. Further the use of the dispersant according to the present invention can provide a toner having a broad selective range of applicable coloring materials and having a high coloring power.

Further features of the present invention will become apparent from the following description of exemplary embodiments.

DESCRIPTION OF THE EMBODIMENTS

Preferred embodiments of the present invention will now be described in detail.
<Compound, Dispersant, and Toner>
Hereinafter, embodiments according to the present invention will be described, but the present invention is not limited to the following embodiments.

The development mechanism of the effect of the dispersant according to the present invention is considered as follows.

The dispersant according to the present invention contains a triketone structure in the adsorption site, and is thus characterized by having a plurality of hydrogen bond points, and being high in the flexibility of the structure. Hence, it is conceivable that the dispersant can be adsorbed through a plurality of points thereof to a coloring material, and that the direction of the adsorption can be varied adjustably to functional groups of the coloring material. It is further conceivable that the adsorption site of the compound intramolecularly causes keto-enol isomerization as shown in the following formula to improve the planarity of the adsorption site to thereby more enhance the adsorption power by the π-π interaction between double bond sites and the coloring material.

The adsorption site with the coloring material includes a compound represented by the formula (1).

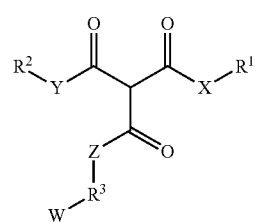

(1)

wherein X, Y and Z are each independently —O—, a methylene group or —$NR^4$—;
$R^4$ represents hydrogen or a straight-chain or branched-chain alkyl group having 1 to 4 carbon atoms;
$R^1$ represents an unsubstituted or substituted phenyl group, a polycyclic aromatic group, or a heterocyclic group;
$R^2$ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond or an amide bond;
$R^3$ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond or an amide bond;

W represents a reactive group or a polymerizable functional group capable of being incorporated in a polymer moiety;

a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group or a ureido group;

the polycyclic aromatic group is a group derived from naphthalene, anthracene, phenanthrene or anthraquinone by removing one hydrogen atom therefrom; and the heterocyclic group is a group derived from imidazole, oxazole, thiazole, pyridine, indole, benzimidazole, benzimidazolinone or phthalimide by removing one hydrogen atom therefrom.

The compound represented by the formula (1) and the structure represented by the formula (3), therefore, can take tautomers as shown in the following formula. These tautomers are also in the scope of the present invention.

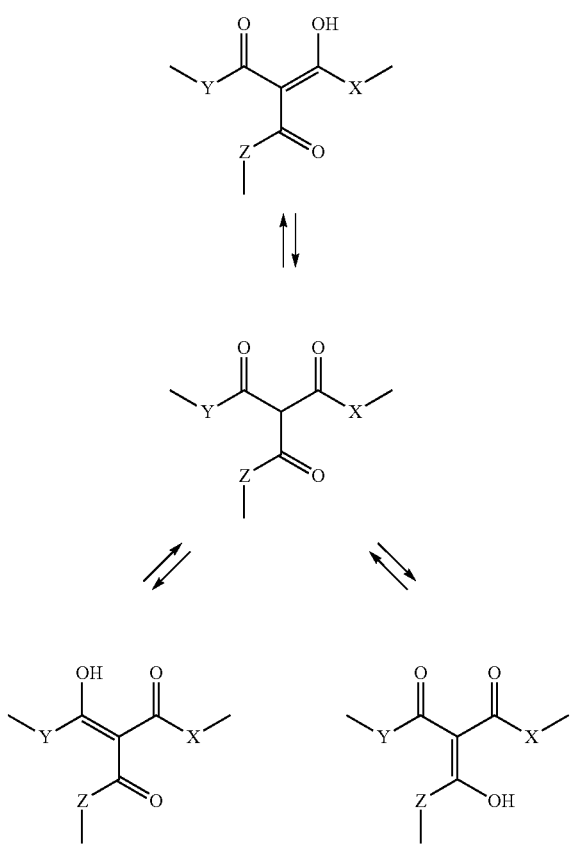

It is conceivable that the adsorption action of the adsorption site in the present invention is, as described above, caused by the hydrogen bond action by polar groups such as ketone, amide and ester groups, and the π-π interaction originated from double bonds and aromatic sites. A dispersant to be used in the present invention has a structure in which a structure represented by the formula (3) or a tautomer thereof is bonded with a polymer moiety.

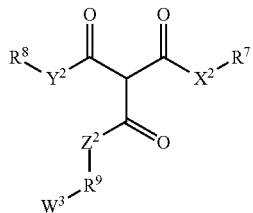

wherein $X^2$, $Y^2$ and $Z^2$ are each independently —O—, a methylene group or —$NR^{10}$—;

$R^{10}$ represents hydrogen or a straight-chain or branched-chain alkyl group having 1 to 4 carbon atoms;

$R^7$ represents an unsubstituted or substituted phenyl group, a polycyclic aromatic group, or a heterocyclic group;

$R^8$ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond or an amide bond;

$R^9$ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond or an amide bond;

$W^3$ represents a linking moiety to the polymer moiety;

a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group or a ureido group;

the polycyclic aromatic group is a group derived from naphthalene, anthracene, phenanthrene or anthraquinone by removing one hydrogen atom therefrom; and the heterocyclic group is a group derived from imidazole, oxazole, thiazole, pyridine, indole, benzimidazole, benzimidazolinone or phthalimide by removing one hydrogen atom therefrom.

$R^7$ in the formula (3) is mainly a site bearing the π-π interaction with a coloring material. Hence, $R^7$ may be a compound having π planarity. Among these, a heterocyclic compound or an aromatic compound substituted with a polar group is preferable, since concurrently having the π planarity and the hydrogen bonding property. The best structure of $R^7$ is a benzimidazolinone structure, which exhibits a high adsorbability to a coloring material and improves the coloring power.

$R^8$ may be by incorporation of a compound having the π planarity to complement the adsorbability to the coloring material, or may be by incorporation of a structure of regulating the solubility to a disperse medium, such as an alkyl group. At this time, the structure can be a structure of not being bulky in order not to inhibit the adsorption to the coloring material. Specifically, $R^8$ is an alkyl group having 1 to 12 carbon atoms or a benzyl group, preferably an alkyl group having 2 to 12 carbon atoms, and more preferably an alkyl group having 2 to 8 carbon atoms. In the case of these structures, since the adsorptivity rate to a coloring material can be maintained, a good coloring power can easily be obtained.

$R^9$ may be any difunctional group, but is preferably an alkylene group having 2 to 4 carbon atoms. When $R^9$ is an alkylene group having 2 to 4 carbon atoms, the cohesion of the adsorption site can be suppressed to easily improve the coloring power, since the adsorption site exhibits a good solubility.

$X^2$, $Y^2$ and $Z^2$ may be each any divalent linking group, but when among $X^2$, $Y^2$ and $Z^2$, two or more groups thereof are —NH—, the case is preferable because the structural stability of the compound is improved. Particularly the case where $X^2$ and $Z^2$ are —NH— is preferable. The reason is that in the case where $X^2$ is —NH—, an amide bond is formed, which is advantageous to the adsorption to a coloring material. Further $Z^2$ can be —NH— from the viewpoint of the production. Here, as $Y^2$, —O— is best from the viewpoint of diversifying the structure of $R^8$ because there are many commercially available reagents producing —O—. $W^3$ is a linking moiety to a polymer moiety, and can be an amide bond or an ester bond from the viewpoint of the production easiness.

From the above, the adsorption site of the dispersant according to the present invention can have a structure represented by the following formula (4).

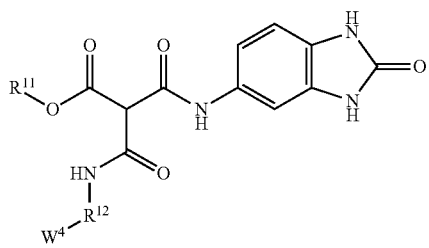

(4)

wherein $R^{11}$ represents an alkyl group having 2 to 12 carbon atoms or a benzyl group, and $R^{11}$ is more preferably an alkyl group having 2 to 8 carbon atoms;

$R^{12}$ represents an alkylene group having 2 to 4 carbon atoms; and $W^4$ represents a linking moiety to a polymer moiety, and the linking moiety is an ester bond or an amide bond.

Here, since the structure represented by the formula (4) can assume tautomers as seen in the following formulae, these tautomers are also in the scope of the present invention.

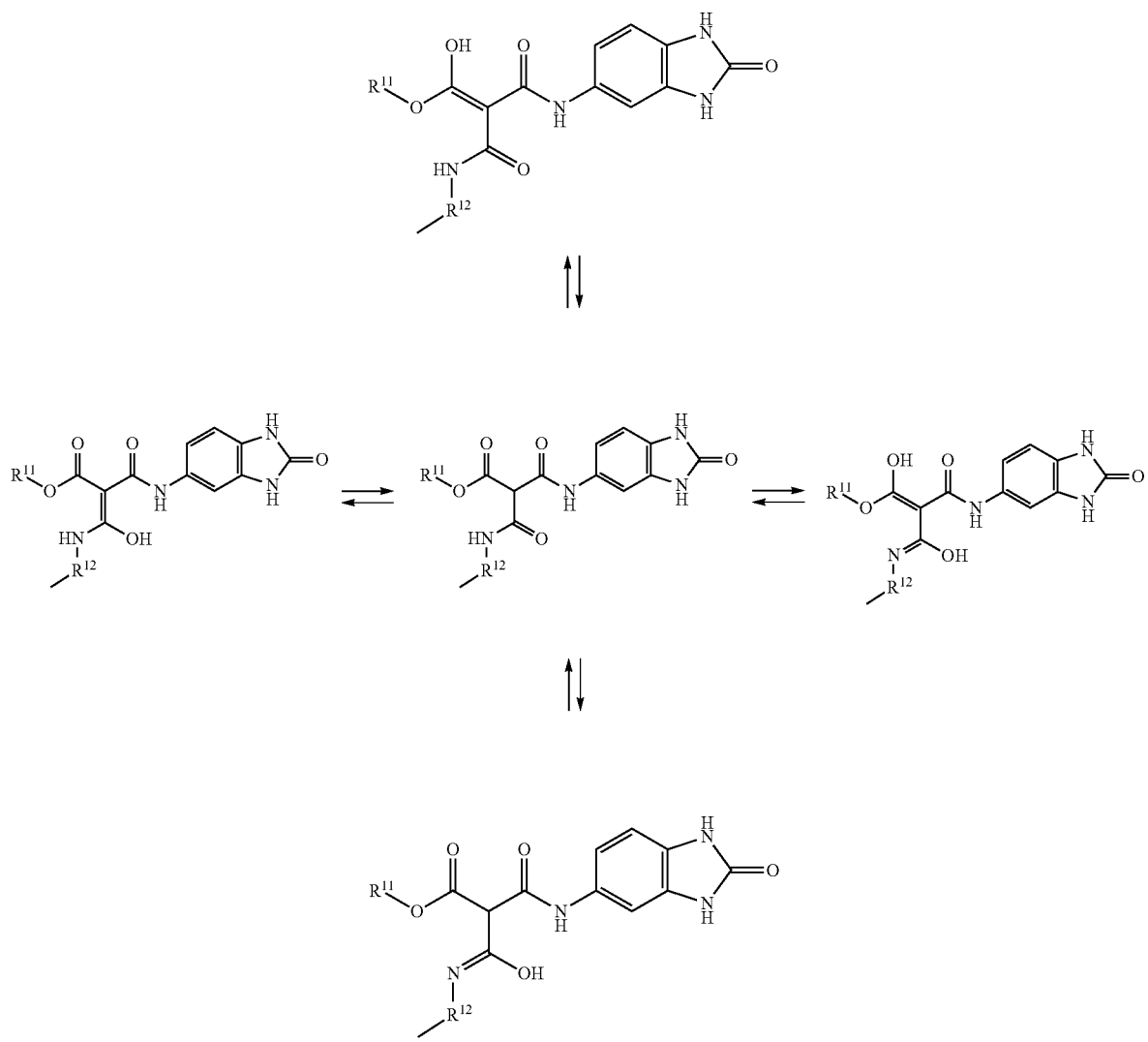

In the case where the adsorption site has the structure of the formula (4), the adsorbability to a coloring material improves, since the stability of the compound improves for the above-mentioned reason. Consequently, it becomes easy for a good coloring power to be provided.

Further the compound represented by the above formula (1) can be a compound represented by the formula (2).

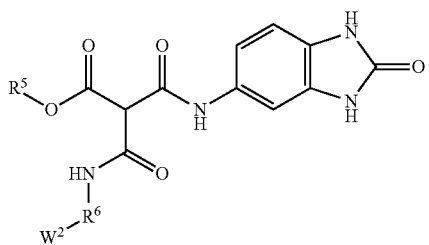

(2)

wherein $R^5$ represents an alkyl group having 2 to 12 carbon atoms or a benzyl group, and $R^5$ is more preferably an alkyl group having 2 to 8 carbon atoms;
$R^6$ represents an alkylene group having 2 to 4 carbon atoms; and
$W^2$ represents an amino group, an acryloyloxy group, a methacryloyloxy group, an acryloylamino group or a methacryloylamino group, and $W^2$ is more preferably an acryloyloxy group or a methacryloyloxy group.

From the above, preferable structure examples of the structure represented by the formula (3) are structures represented by the following formulae (6) to (8), but the adsorption site of the dispersant to be used in the present invention is not limited thereto.

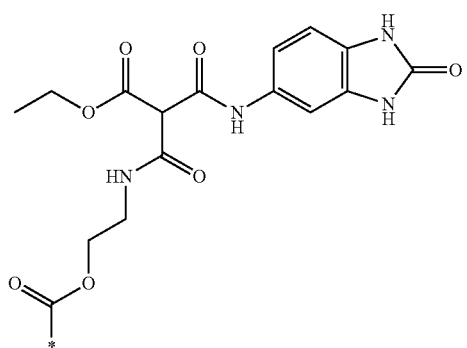

(6)

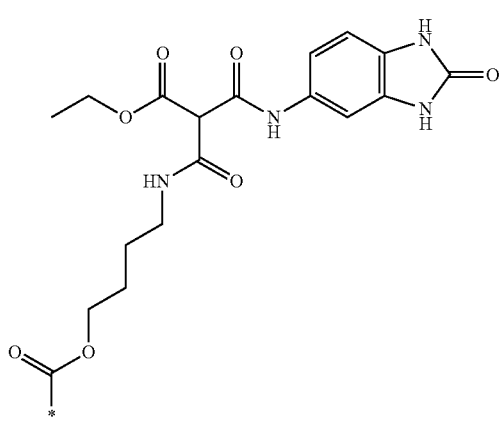

(7)

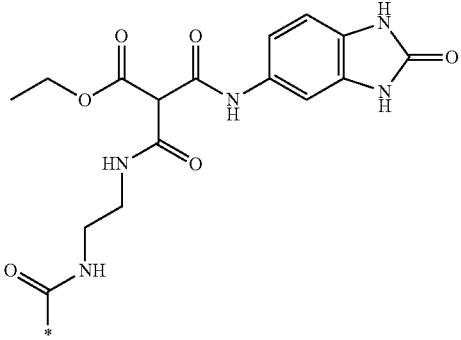

(8)

In the formulae (6) to (8), * each represent a linking moiety to a polymer moiety.

The dispersant to be used in the present invention can be used singly out of the above-mentioned adsorption sites or in a combination of two or more thereof.

Then, a polymer moiety of the dispersion site will be described specifically.

The polymer moiety according to the present invention may be a polymer exhibiting the affinity for a disperse medium, and a known polymer can be selected. The specific examples of the polymer include vinylic polymers using vinylic monomers, polyesters, polyethers, polyamides, and composite polymers in which these partial structures coexist.

In the present invention, the polymer moiety can be a vinylic copolymer structure or a polyester structure, which is obtained by using versatile monomers. By arbitrary selecting monomers from various monomer species, the SP value (solubility parameter) of a dispersion site polymer is enabled to approach to that of a medium, and thus the dispersion effect is easily developed. Further in the case of a vinylic copolymer structure, the production of a dispersant becomes easy when a compound having the adsorption site has a polymerizable functional group.

In the case where the dispersion site of the dispersant according to the present invention is the vinylic copolymer structure, the structure can have at least either of a unit B originated from a compound B which is an aromatic vinyl monomer or a unit C originated from a compound C which is an acrylic acid-based monomer or a methacrylic acid-based monomer.

The compound B constituting the unit B can be an aromatic vinyl monomer having affinity for a medium to disperse a coloring material; and specific examples of the compound B include styrene, vinyltoluene and α-methylstyrene. These compounds B can be used singly or in a combination of two or more. The compound B may be selected suitably depending on a medium to be used.

On the other hand, the compound C constituting the unit C can be an acrylic acid-based monomer or a methacrylic acid-based monomer having affinity for a medium to disperse a coloring material. Specific examples of the compound C include acrylic acid-based monomers such as acrylic acid, methyl acrylate, ethyl acrylate, propyl acrylate, butyl acrylate, 2-ethylhexyl acrylate, octyl acrylate, dodecyl acrylate, stearyl acrylate, behenyl acrylate, hydroxyethyl acrylate, hydroxypropyl acrylate, glycidyl acrylate and benzyl acrylate; and methacrylic acid-based monomers such as methacrylic acid, methyl methacrylate, ethyl methacrylate, propyl methacrylate, butyl methacrylate, 2-ethylhexyl methacrylate, octyl methacrylate, dodecyl methacrylate, stearyl methacrylate, behenyl methacrylate, hydroxyethyl methacrylate, hydroxypropyl methacrylate, glycidyl methacrylate and benzyl methacrylate. These compounds C can be used singly or in a combination of two or more. The compound C may be selected suitably depending on a medium to be used.

Further the dispersant can meet a relation of the following formula (5), wherein the content (parts by mole) of the structure represented by the formula (3), which is the adsorption site according to the present invention, is represented by "a"; the content (parts by mole) of the unit B in terms of the molecular weight of the compound B is represented by "b"; and the content (parts by mole) of the unit C in terms of the molecular weight of the compound C is represented by "c".

$$0.01 \leq a/(b+c) \leq 2.00 \tag{5}$$

By meeting the relation of the formula (5), the high adsorption power to a coloring material and the stable dispersibility of the coloring material in a medium can be attained, since the balance between the amount of the adsorption site and the amount of the dispersion site becomes good.

Values of the above-mentioned a, b and c can be calculated by the GPC (gel permeation chromatography) measurement and the NMR measurement of the dispersant. Specifically, the values can be calculated from a weight-average molecular weight of the dispersant as calculated by GPC and a ratio of each unit as calculated by $^1$H-NMR.

On the other hand, in the case where the dispersion site (polymer moiety) of the dispersant according to the present invention is a polyester structure, the polyester structure has a unit originated from a polycarboxylic acid, and a unit originated from a polyol.

Specific examples of the polycarboxylic acid include dicarboxylic acids such as oxalic acid, glutaric acid, succinic acid, maleic acid, adipic acid, β-methyladipic acid, azelaic acid, sebacic acid, nonanedicarboxylic acid, decanedicarboxylic acid, undecanedicarboxylic acid, dodecanedicarboxylic acid, fumaric acid, citraconic acid, diglycolic acid, cyclohexane-3,5-diene-1,2-carboxylic acid, hexahydroterephthalic acid, malonic acid, pimelic acid, phthalic acid, isophthalic acid, terephthalic acid, tetrachlorophthalic acid, chlorophthalic acid, nitrophthalic acid, p-carboxyphenylacetic acid, p-phenylenediacetic acid, m-phenylenediglycolic acid, p-phenylenediglycolic acid, o-phenylenediglycolic acid, diphenylacetic acid, diphenyl-p,p'-dicarboxylic acid, naphthalene-1,4-dicarboxylic acid, naphthalene-1,5-dicarboxylic acid, naphthalene-2,6-dicarboxylic acid, anthracenedicarboxylic acid and cyclohexanedicarboxylic acid. Examples of polycarboxylic acids other than dicarboxylic acids include trimellitic acid, pyromellitic acid, naphthalenetricarboxylic acid, naphthalenetetracarboxylic acid, pyrenetricarboxylic acid and pyrenetetracarboxylic acid.

The examples of the polyol include ethylene glycol, diethylene glycol, triethylene glycol, 1,2-propylene glycol, 1,3-propylene glycol, 1,4-butanediol, neopentyl glycol, 1,4-butenediol, 1,5-pentanediol, 1,6-hexanediol, 1,4-cyclohexanedimethanol, dipropylene glycol, polyethylene glycol, polypropylene glycol, polytetramethylene glycol, sorbitol, 1,2,3,6-hexanetetrol, 1,4-sorbitan, pentaerythritol, dipentaerythritol, tripentaerythritol, 1,2,4-butanetriol, 1,2,5-pentanetriol, glycerol, 2-methylpropanetriol, 2-methyl-1,2,4-butanetriol, trimethylolethane, trimethylolpropane, 1,3,5-trihydroxymethylbenzene, bisphenol A, bisphenol A ethylene oxide adducts, bisphenol A propylene oxide adducts, hydrogenated bisphenol A, hydrogenated bisphenol A ethylene oxide adducts and hydrogenated bisphenol A propylene oxide adducts.

Further the dispersion site (polymer moiety) may be a composite polymer having a polyester structure and a vinylic copolymer structure. Specifically, in a case where the vinylic polymer structure is grafted to a polyester main chain, the examples of the polymer moiety include a composite polymer having a structure in which the polyester structure and the vinylic polymer structure are bonded in blocks. At this time, the adsorption site (structure represented by the formula (3)) may be bonded to either of the polyester structure site or the vinylic polymer site.

(Molecular Weight of a Dispersant)

The weight-average molecular weight of the dispersant to be used in the present invention is preferably in the range of 5,000 or higher and 200,000 or lower. In the case where the weight-average molecular weight is 5,000 or higher, since the coloring material cohesion can be suppressed by the excluded volume effect of the dispersant, the coloring power is easily improved. On the other hand, in the case where the weight-average molecular weight is 200,000 or lower, since the crosslinking among the coloring material through the dispersant hardly occurs, the coloring power is easily improved. The weight-average molecular weight is more preferably in the range of 10,000 or higher and 50,000 or lower. The weight-average molecular weight of the dispersant can be controlled by altering the temperature and the reaction time during the polymerization.

(Coloring Material)

Examples of coloring materials applicable to the dispersant according to the present invention include known insoluble coloring materials. Specific examples of the coloring material include black/yellow/magenta/cyan pigments and oil-soluble dyes. Examples of suitable coloring materials to which the dispersant according to the present invention is applicable include conventionally known insoluble coloring materials. Specific examples of the coloring material include black/yellow/magenta/cyan pigments and oil-soluble dyes.

Specific examples of black pigments and oil-soluble dyes include carbon black. Further, specific examples thereof include pigments, by trade names, such as: Raven 760 Ultra, Raven 1060 Ultra, Raven 1080, Raven 1100 Ultra, Raven 1170, Raven 1200, Raven 1250, Raven 1255, Raven 1500, Raven 2000, Raven 2500 Ultra, Raven 3500, Raven 5250, Raven 5750, Raven 7000, Raven 5000 ULTRAII and Raven 1190 ULTRAII (the foregoing, manufactured by Columbian Chemicals Co.);

Black Pearls L, MOGUL-L, Regal 400R, Regal 660R, Regal 330R, Monarch 800, Monarch 880, Monarch 900, Monarch 1000, Monarch 1300 and Monarch 1400 (the foregoing, manufactured by Cabot Corp.);

Color Black FW1, Color Black FW2, Color Black FW200, Color Black 18, Color Black S160, Color Black S170, Special Black 4, Special Black 4A, Special Black 6, Special Black 550, Printex 35, Printex 45, Printex 55, Printex 85, Printex 95, Printex U, Printex 140U, Printex V and Printex 140V (the foregoing, manufactured by Degussa GmbH); and No. 25, No. 33, No. 40, No. 45, No. 47, No. 52, No. 900, No. 970, No. 2200B, No. 2300, No. 2400B, MCF-88, MA600, MA77, MA8, MA100, MA230 and MA220 (the foregoing, manufactured by Mitsubishi Chemical Corp.), and include C.I. Solvent Blacks 3, 5, 7, 8, 14, 17, 19, 20, 22, 24, 26, 27, 28, 29, 43 and 45.

Examples of yellow pigments and oil-soluble dyes include condensed azo compounds, isoindolinone compounds, anthraquinone compounds, azo metal complexes, methine compounds and allylamide compounds. Examples of the yellow pigments and oil-soluble dyes more specifically include pigments such as C.I. Pigment Yellows 12, 13, 14, 15, 17, 62, 74, 83, 93, 94, 95, 109, 110, 111, 128, 129, 147, 168 and 180; and oil-soluble dyes such as C.I. Solvent Yellows 1, 2, 3, 13, 14, 19, 21, 22, 29, 36, 37, 38, 39, 40, 42, 43, 44, 45, 47, 62, 63, 71, 76, 79, 81, 82, 83:1, 85, 86, 88 and 151.

Examples of magenta pigments and oil-soluble dyes include condensed azo compounds, diketopyrrolopyrrole compounds, anthraquinone compounds, quinacridone compounds, basic dye lake compounds, naphthol compounds, benzimidazolone compounds, thioindigo compounds and perylene compounds. Examples of the Magenta pigments and oil-soluble dyes more specifically include pigments such as C.I. Pigment Reds 2, 3, 5, 6, 7, 23, 48:2, 48:3, 48:4, 57:1, 81:1, 122, 144, 146, 166, 169, 177, 184, 185, 202, 206, 220, 221 and 254; and oil-soluble dyes such as C.I. Solvent Reds 8, 27, 35, 36, 37, 38, 39, 40, 49, 58, 60, 65, 69, 81, 83:1, 86, 89, 91, 92, 97, 99, 100, 109, 118, 119, 122, 127 and 218.

Examples of cyan pigments and oil-soluble dyes include copper phthalocyanine compounds and derivatives thereof, anthraquinone compounds, and basic dye lake compounds. Examples of the cyan pigments and oil-soluble dyes more specifically include pigments such as C.I. Pigment Blues 1, 7, 15, 15:1, 15:2, 15:3, 15:4, 60, 62 and 66; and oil-soluble dyes such as C.I. Solvent Blues 14, 24, 25, 26, 34, 37, 38, 39, 42, 43, 44, 45, 48, 52, 53, 55, 59, 67 and 70. These pigments and oil-soluble dyes can be used singly or in a combination of two or more.

(Medium)

Use of the dispersant according to the present invention enables production of a coloring material dispersion containing a medium and a coloring material dispersed in the medium by the dispersant. The kind of the medium to disperse the coloring material is not especially limited, and a water-insoluble organic solvent, water, a water-soluble organic solvent, a polymerizable monomer, a resin or the like, which is conventionally used for inks, coating materials and toners, can be used singly or as a mixture thereof.

Specific examples of the water-insoluble organic solvent usable as the medium include toluene, methyl ethyl ketone, chloroform, ethyl acetate, hexane and heptane.

Specific examples of the water-soluble organic solvent usable as the medium include lower alcohols such as methyl alcohol, ethyl alcohol, n-propyl alcohol, isopropyl alcohol, n-butyl alcohol, sec-butyl alcohol and tert-butyl alcohol; diols such as ethylene glycol, diethylene glycol, triethylene glycol, tetraethylene glycol, propylene glycol, dipropylene glycol, tripropylene glycol, 1,2-butanediol, 1,3-butanediol, 1,4-butanediol, thiodiglycol and 1,4-cyclohexanediol; triols such as 1,2,4-butanetriol, 1,2,6-hexanetriol and 1,2,5-pentanetriol; hindered alcohols such as trimethylolpropane, trimethylolethane, neopentyl glycol and pentaerythritol; glycol ethers such as ethylene glycol monomethyl ether, ethylene glycol monoethyl ether, ethylene glycol monoisopropyl ether, ethylene glycol monoallyl ether, diethylene glycol monomethyl ether, diethylene glycol monoethyl ether, diethylene glycol monobutyl ether, triethylene glycol monomethyl ether, triethylene glycol monoethyl ether, propylene glycol monomethyl ether and dipropylene glycol monomethyl ether; and glycerol, dimethyl sulfoxide, glycerol monoallyl ether, polyethylene glycol, N-methyl-2-pyrrolidone, 2-pyrrolidone, γ-butyrolactone, 1,3-dimethyl-2-imidazolidinone, sulfolane, β-dihydroxyethylurea, urea, acetonylacetone, dimethylformamide, dimethylacetamide, acetone, diacetone alcohol, pyridine, dioxane, and tetrahydrofuran.

Specific examples of the polymerizable monomer usable as the medium include styrene; styrenic monomers such as o-(m-, p-)methylstyrene and m-(p-)ethylstyrene; acrylate ester monomers and methacrylate ester monomers such as methyl acrylate, methyl methacrylate, ethyl acrylate, ethyl methacrylate, propyl acrylate, propyl methacrylate, butyl acrylate, butyl methacrylate, octyl acrylate, octyl methacrylate, dodecyl acrylate, dodecyl methacrylate, stearyl acrylate, stearyl methacrylate, behenyl acrylate, behenyl methacrylate, 2-ethylhexyl acrylate, 2-ethylhexyl methacrylate, dimethylaminoethyl acrylate, dimethylaminoethyl methacrylate, diethylaminoethyl acrylate and diethylaminoethyl methacrylate; enic monomers such as butadiene, isoprene and cyclohexene, acrylonitrile, methacrylonitrile, and amide-based monomers such as acrylic acid amide and methacrylic acid amide.

Specific examples of the resin usable as the medium include known resins such as vinylic resins, maleic acid copolymer resins, polyester resins, epoxy resins and composite resins in which partial structures thereof are bound.

(Additives)

In the coloring material dispersion obtained by using the dispersant according to the present invention, in addition to the above-mentioned components, various types of additives, such as a surfactant, a pH adjuster, an antioxidant and a fungicide, may be added.

(Use Ratio of the Dispersant)

The amount of the dispersant to be used for dispersing a coloring material as described above in a medium is preferably 0.05 to 200 parts, and more preferably 0.1 to 100 parts with respect to 100 parts of the coloring material, which easily develops the effect of the dispersant according to the present invention.

(Toner)

The toner according to the present invention will be described. The toner according to the present invention is a toner having a toner particle containing a binder resin, a coloring material and the dispersant.

As a coloring material usable for the toner according to the present invention, the same coloring material as the coloring material applicable to the dispersant according to the present invention can be used.

Further as the binder resin to be used for the toner according to the present invention, known resins, such as vinylic resins, maleic acid copolymer resins, polyester resins, epoxy resins and composite resins in which partial structures thereof are bound, can be used.

The vinylic resin is a resin obtained by polymerizing a radically polymerizable vinylic monomer.

Examples of the vinylic monomer include styrene derivatives such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene and p-phenylstyrene;
acrylic polymerizable monomers such as methyl acrylate, ethyl acrylate, n-propyl acrylate, iso-propyl acrylate, n-butyl acrylate, iso-butyl acrylate, tert-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethyl phosphate ethyl acrylate, diethyl phosphate ethyl acrylate, dibutyl phosphate ethyl acrylate and 2-benzoyloxyethyl acrylate; and methacrylic polymerizable monomers such as methyl methacrylate, ethyl methacrylate, n-propyl methacrylate, iso-propyl methacrylate, n-butyl methacrylate, iso-butyl methacrylate, tert-butyl methacrylate, n-amyl methacrylate, n-hexyl methacrylate, 2-ethylhexyl methacrylate, n-octyl methacrylate, n-nonyl methacrylate, diethyl phosphate ethyl methacrylate and dibutyl phosphate ethyl methacrylate. Examples of polyfunctional polymerizable monomers include diethylene glycol diacrylate, triethylene glycol diacrylate, tetraethylene glycol diacrylate, polyethylene glycol diacrylate, 1,6-hexanediol diacrylate, neopentyl glycol diacrylate, tripropylene glycol diacrylate, polypropylene glycol diacrylate, 2,2'-bis(4-(acryloxydiethoxy)phenyl)propane, trimethylolpropane triacrylate, tetramethylolmethane tetraacrylate, ethylene glycol dimethacrylate, diethylene glycol dimethacrylate, triethylene glycol dimethacrylate, tetraethylene glycol dimethacrylate, polyethylene glycol dimethacrylate, 1,3-butylene glycol dimethacrylate, 1,6-hexanediol dimethacrylate, neopentyl glycol dimethacrylate, polypropylene glycol dimethacrylate, 2,2'-bis(4-(methacryloxydiethoxy)phenyl)propane, 2,2'-bis(4-(methacryloxypolyethoxy)phenyl)propane, trimethylolpropane trimethacrylate, tetramethylolmethane tetramethacrylate, divinylbenzene, divinylnaphthalene and divinyl ether. These can be used singly or in a combination of two or more.

Further as monomers to be used for formation of the polyester resin, polycarboxylic acids and polyols which were described in the case where the dispersion site of the dispersant was a polyester structure are used.

Further examples of the binder resins usable in the present invention include composite polymers in which partial structures of the polymers coexist. Examples of the binder resins specifically include a composite polymer of a case where the vinylic polymer structure is grafted to a polyester main chain, and a composite polymer having a structure in which the polyester structure and the vinylic polymer structure are bonded in blocks.

(Production Method of the Dispersant)

Then, a production method of the dispersant according to the present invention will be described.

The dispersant to be used in the present invention can be obtained by copolymerizing the compound according to the present invention in which a polymerizable group is incorporated to the adsorption site with a monomer constituting the dispersion site, or by adding the compound according to the present invention to a previously polymerized polymer.

In either production method, the dispersant can be obtained by known synthesis methods and polymerization methods.

The dispersant can be synthesized, for example, according to the following scheme.

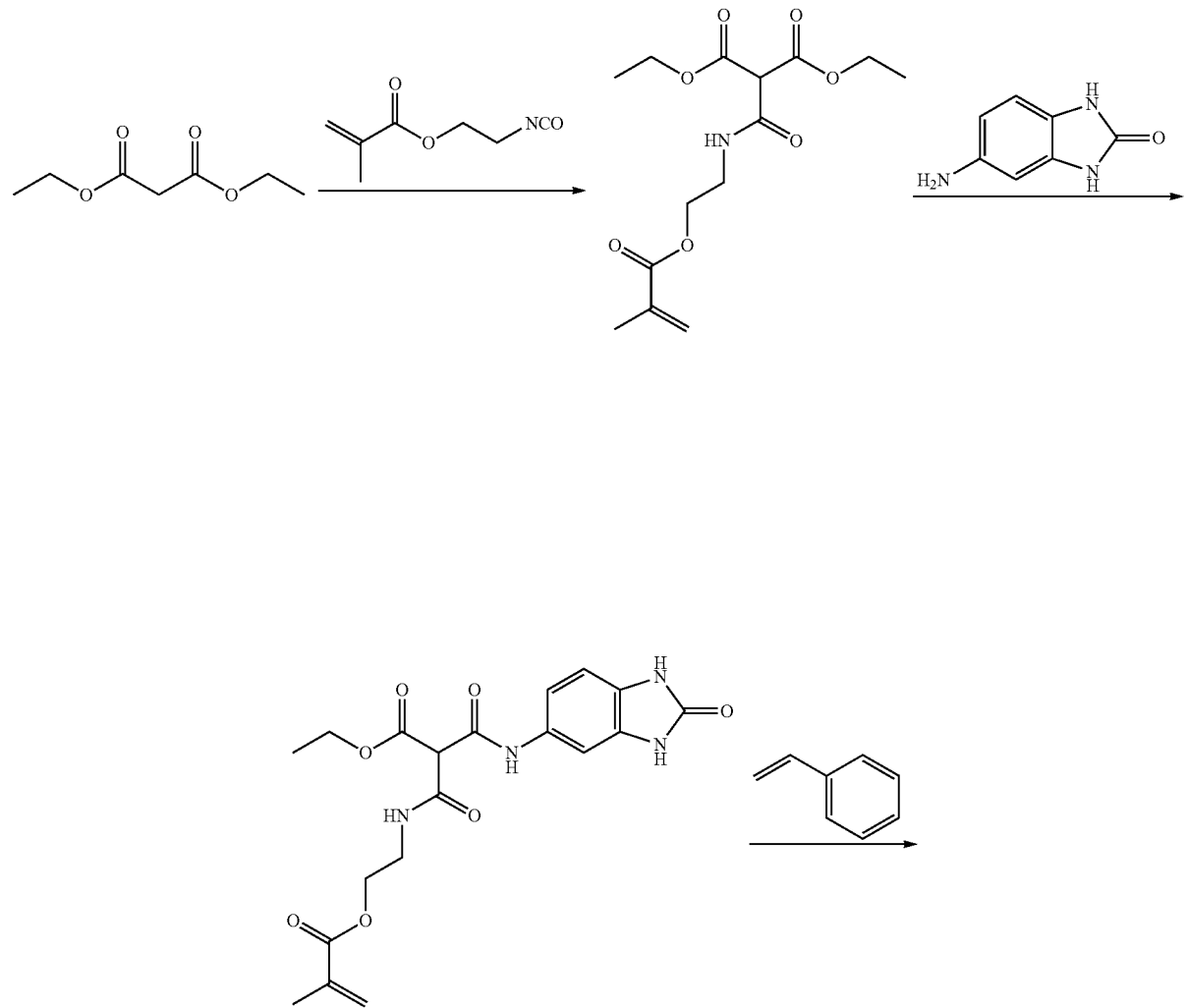

-continued

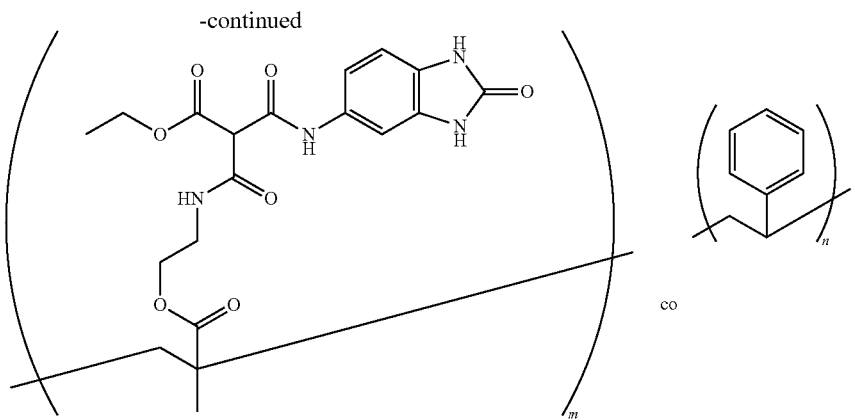

In the above scheme, "-co-" means copolymerization; and m and n represent repeating of corresponding structural units.

The adsorption site having a polymerizable functional group incorporated therein in the above scheme can be polymerized with a dispersion site monomer by a conventionally known method such as radical polymerization, living radical polymerization, anionic polymerization or cationic polymerization to thereby make a dispersant. In the dispersant, adsorption sites and dispersion sites may be present in a random state, or may be present in a block state.

The reaction temperature, the reaction time, and the kinds of a solvent, a catalyst and the like to be used in each step, a refining method after the synthesis, and the like may suitably be selected depending on target materials. The molecular structure of the synthesized adsorption site and the physical properties of the polymerized dispersant can be identified by using NMR (nuclear magnetic resonance apparatus), IR (infrared spectrometer), MS (mass spectrometer), GPC (gel permeation chromatography), and the like.

On the other hand, in the case where the compound according to the present invention is added to a previously polymerized polymer, it is necessary that a functional group addition-reactive with the compound is previously made to be present on the polymer before the addition, which can be performed by utilizing known methods. For example, in the case where a raw material polymer has a carboxy group, in the compound according to the present invention, W in the formula (1) can be a reactive group such as an amino group or a hydroxyl group. By acid-chlorinating the carboxy group with thionyl chloride or the like, a compound having an amino group or a hydroxyl group can be added.

(Production Method of the Coloring Material Dispersion)

The coloring material dispersion can be produced, for example, by kneading or crushing the dispersant according to the present invention and a coloring material in a medium. Here, the production of the coloring material dispersion by a method described below is preferable because the adsorbability of the dispersant to a coloring material is more improved to allow the stability of the coloring material dispersion to become high.

First, the dispersant and a coloring material are mixed in a medium, and subjected to a mechanical shearing force using a dispersing machine to cause the adsorption site originated from the compound in the dispersant to be adsorbed on the coloring material surface to thereby disperse the coloring material into a uniform microparticle. In the case where the medium is an organic solvent, as required, by removing the organic solvent by a usual method such as pressure reduction, the dispersant may be immobilized on the coloring material surface. Further in the case where the medium is a polymerizable monomer, as required, by polymerizing the polymerizable monomer, the dispersant may be immobilized on the coloring material surface. Further as required, filtration, centrifugation, drying and the like are carried out to thereby obtain the coloring material dispersion.

(Dispersing Machine)

The kind of a dispersing machine to be used in production of the coloring material dispersion is not especially limited, and a usually used dispersion machine can be used. Specific examples of the dispersing machine include a ball mill, a bead mill, an ultrasonic disperser, a paint shaker, a sand mill, a homogenizer, a vibration ball mill, a roll mill, a homomixer, "Microfluidizer" by trade name (manufactured by Microfluidics International Corp.), "Nanomizer" by trade name (manufactured by Nanomizer Inc.), and a twin-screw kneader.

(Production Method of the Toner)

Then, a production method of the toner according to the present invention will be described.

The toner particle according to the present invention can be produced by a known method. Methods usable are, for example, a suspension polymerization method involving suspending, in an aqueous medium, a polymerizable monomer composition containing a polymerizable monomer for obtaining a binder resin, a coloring material, the dispersant, and as required a release agent and the like, and polymerizing the polymerizable monomer to thereby form the binder resin; a kneading crushing method in which various toner constituting materials are kneaded, crushed and classified; an emulsion aggregation method involving mixing a dispersion liquid having a binder resin emulsified and dispersed therein, with a dispersion liquid of a coloring material and the dispersant, and as required, a dispersion liquid of a release agent and the like, and aggregated and thermally fused these materials to thereby obtain a toner particle; an emulsion polymerization aggregation method involving mixing a dispersion liquid formed by emulsion-polymerizing a polymerizable monomer of a binder resin, with a dispersion liquid of a coloring material, and the dispersant, and as required, a dispersion liquid of a release agent and the like, and aggregated and thermally fused these materials to thereby obtain a toner particle; and a dissolution suspension method in which a solution of a binder resin, a coloring material, the dispersant and as required, a release agent and the like is suspended and granulated in an aqueous medium.

Further the toner according to the present invention may contain a charge control agent. Examples of the charge control agent include organometal compounds such as metal salicylate compounds, and charge control resins having a sulfonic acid group or a carboxy group.

In the present invention, in order to improve the image quality of the toner, an external additive can be added externally to the toner particle. As the external additive, an inorganic micropowder such as silica micropowder, titanium oxide micropowder or aluminum oxide micropowder can suitably be used. These inorganic micropowders can be subjected to a hydrophobization treatment with a hydrophobizing agent such as a silane coupling agent, a silicone oil or a mixture thereof. Further the toner according to the present invention may be a toner in which, as required, external additives other than the above are mixed with the toner particle.

The total amount of the inorganic micropowder added can be 1.0 part or larger and 5.0 parts or smaller based on 100.0 parts of the toner particle.

EXAMPLES

Hereinafter, the present invention will be described specifically by way of Examples, but the present invention is not limited thereto. Here, "parts" and "%" in the description are in terms of mass.

<Synthesis of Compounds>

Compounds (A1) to (A17) of structures represented in the following Table 1 were synthesized.

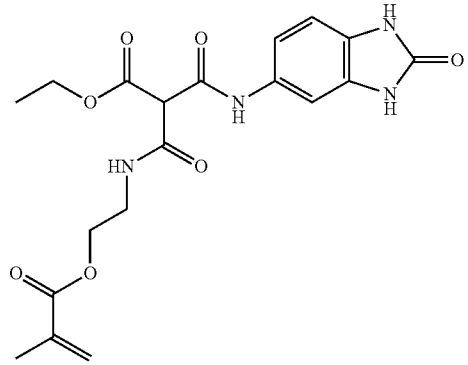

Intermediate (1)

Compound (A1)

TABLE 1

Structures of Compounds

| Compound | R¹ | R² | R³ | X | Y | Z | W |
|---|---|---|---|---|---|---|---|
| A1 | benzimidazolinone | —CH2CH3 | —(CH2)2— | NH | O | NH | methacryloyloxy |
| A2 | phenylureido | —CH2CH3 | —(CH2)2— | NH | O | NH | methacryloyloxy |
| A3 | phenylureido | —CH2CH3 | —(CH2)2— | NH | O | NH | amino |
| A4 | benzimidazolinone | —CH2CH3 | —(CH2)2— | NH | O | NH | methacryloylamino |
| A5 | benzimidazolinone | —(CH2)3CH3 | —(CH2)2— | NH | NH | NH | methacryloyloxy |
| A6 | benzimidazolinone | benzimidazolinone | —(CH2)2— | NH | NH | NH | methacryloyloxy |
| A7 | benzimidazolinone | —(CH2)3CH3 | —(CH2)2— | NH | O | NH | methacryloyloxy |
| A8 | benzimidazolinone | —(CH2)7CH3 | —(CH2)2— | NH | O | NH | methacryloyloxy |
| A9 | benzimidazolinone | —(CH2)11CH3 | —(CH2)2— | NH | O | NH | methacryloyloxy |
| A10 | benzimidazolinone | benzyl | —(CH2)2— | NH | O | NH | methacryloyloxy |
| A11 | benzimidazolinone | —CH2CH3 | —(CH2)2— | NH | O | NH | acryloyloxy |
| A12 | benzimidazolinone | —CH2CH3 | —(CH2)2— | NH | O | NH | amino |
| A13 | benzimidazolinone | —CH2CH3 | —(CH2)2— | NH | O | NH | hydroxy |
| A14 | benzimidazolinone | —CH2CH3 | —(CH2)4— | NH | O | NH | methacryloyloxy |
| A15 | benzimidazolinone | —CH2CH3 | —(CH2)2— | O | O | NH | methacryloyloxy |
| A16 | benzimidazolinone | —CH2CH3 | —(CH2)2— | NH | O | O | methacryloyloxy |
| A17 | phenyl | —CH2CH3 | —(CH2)2— | NCH₃ | NCH₃ | NCH₃ | methacryloyloxy |

(Synthesis of Compound (A1))

Compound (A1) was synthesized according to the synthesis scheme shown in the below.

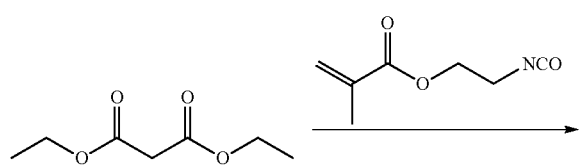

[Synthesis of an Intermediate (1)]

An intermediate (1) was synthesized by reference to the description of a synthesis example 1 in Japanese Patent Application Laid-Open No. H10-316643. Specifically, 20.6 parts (0.129 mol) of diethyl malonate, 19.8 parts (0.128 mol) of 2-methacryloyloxyethyl isocyanate (trade name: "Karenz MOI", manufactured by Showa Denko K.K.), and 0.284 part (1.29 mmol) of 2,6-di-tert-butyl-p-cresol were dissolved in 100 parts (0.942 mol) of xylene, and heated at 60° C. 0.214 part (3.96 mmol) of sodium methoxide was added and the reaction was carried out for 8 hours; and thereafter, 200 parts (11.1 mol) of water was added and the reaction was suspended. The organic layer was extracted and concentrated with toluene, and the obtained residue was crystallized with toluene to thereby obtain an intermediate (1) represented by the above formula.

[Synthesis of Compound (A1)]

19.8 parts (62.8 mmol) of the intermediate (1), 11.4 parts (76.4 mmol) of 5-amino-2-benzimidazolinone and 0.138 part (0.626 mmol) of 2,6-di-tert-butyl-p-cresol were dissolved in 141 parts (1.93 mol) of N,N-dimethylformamide, and reacted under heating and stirring at 80° C. for 6 hours. After the reaction, N,N-dimethylformamide was distilled away under reduced pressure, and 300 parts (16.7 mol) of water was added to the obtained residue. The deposit was filtered to thereby obtain Compound (A1).

(Synthesis of Compound (A2))

Compound (A2) was synthesized according to the following scheme.

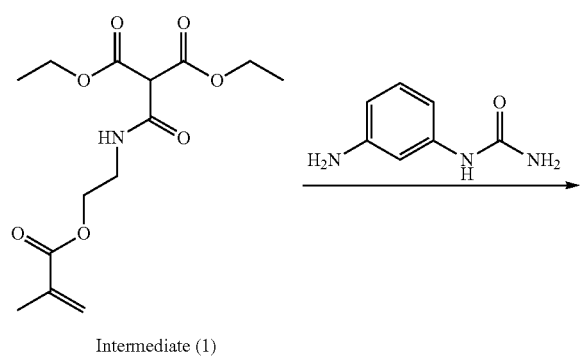

Intermediate (1)

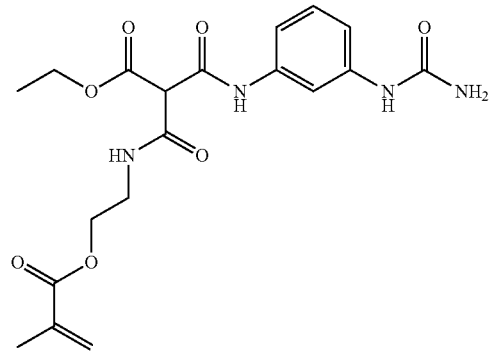

Compound (A2)

Compound (A2) was synthesized by the same method as the above-mentioned synthesis of Compound (A1), except for altering 5-amino-2-benzimidazolinone to 3-aminophenylureido in the synthesis of Compound (A1).

(Synthesis of Compound (A3))

Compound (A3) was synthesized according to the following scheme.

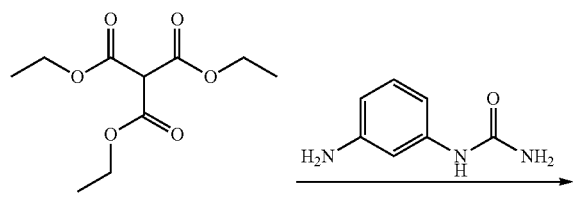

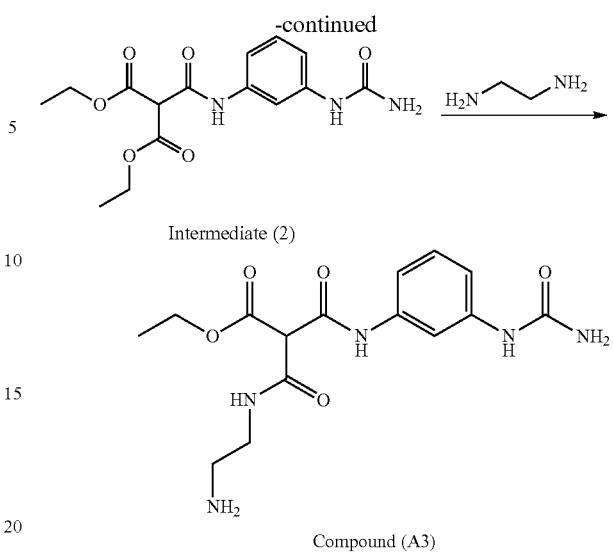

Intermediate (2)

Compound (A3)

14.5 parts (62.4 mmol) of triethyl carboxymalonate, 11.5 parts (76.1 mmol) of 3-aminophenylureido and 0.138 part (0.626 mmol) of 2,6-di-tert-butyl-p-cresol were dissolved in 141 parts (1.93 mol) of N,N-dimethylformamide, and reacted under heating and stirring at 80° C. for 6 hours. After the reaction, N,N-dimethylformamide was distilled away under reduced pressure, and 300 parts (16.7 mol) of water was added to the obtained residue. The deposit was filtered to thereby obtain an intermediate (2).

18.9 parts (56.0 mmol) of the intermediate (2), 50.0 parts (0.684 mol) of N,N-dimethylformamide, 0.124 part (0.563 mmol) of 2,6-di-tert-butyl-p-cresol and 5.05 parts (84.0 mmol) of ethylenediamine were mixed, and reacted under heating and stirring at 80° C. for 6 hours. After the reaction, N,N-dimethylformamide was distilled away under reduced pressure, and 300 parts (16.7 mol) of water was added to the obtained residue. The deposit was filtered to thereby obtain Compound (A3).

(Synthesis of Compound (A4))

Compound (A4) was synthesized according to the following

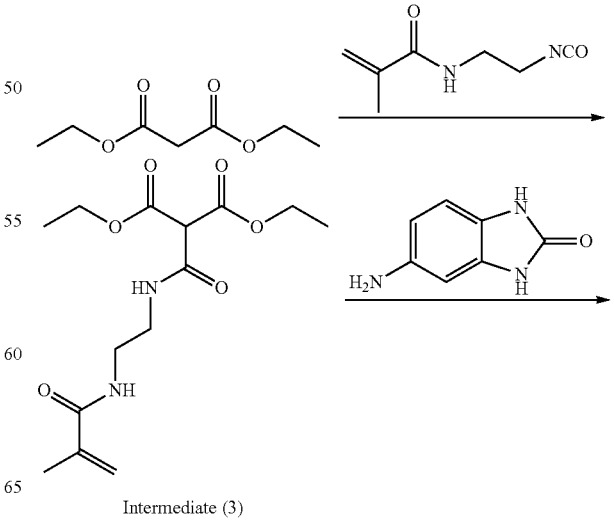

Intermediate (3)

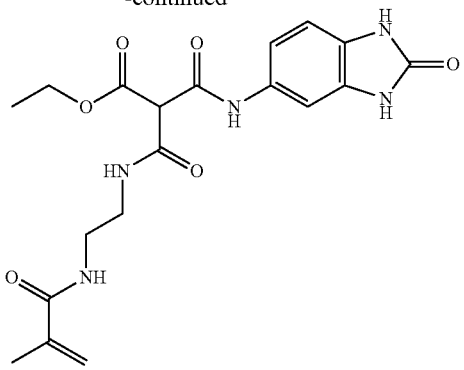

Compound (A4)

An intermediate (3) was synthesized by the same method as the above-mentioned synthesis of the intermediate (1), except for altering 2-methacryloyloxyethyl isocyanate to 2-methacryloylaminoethyl isocyanate.

Compound (A4) was synthesized by the same method as the above-mentioned synthesis of Compound (A1), except for altering the intermediate (1) in the synthesis of Compound (A1) to the intermediate (3).

(Synthesis of Compound (A5))

Compound (A5) was synthesized according to the following scheme.

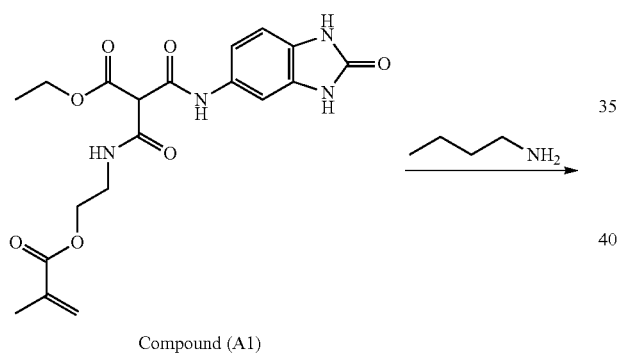

20.0 parts (47.8 mmol) of Compound (A1), 60.0 parts (0.821 mol) of N,N-dimethylformamide, 0.105 part (0.478 mmol) of 2,6-di-tert-butyl-p-cresol and 17.5 parts (0.239 mol) of N-butylamine were mixed, and reacted under heating and stirring at 80° C. for 6 hours. After the reaction, N,N-dimethylformamide was distilled away under reduced pressure, and 300 parts (16.7 mol) of water was added to the obtained residue. The deposit was filtered to thereby obtain Compound (A5).

(Synthesis of Compound (A6))

Compound (A6) was synthesized according to the following scheme.

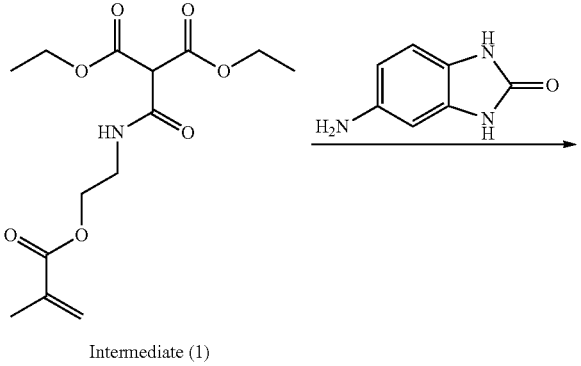

Intermediate (1)

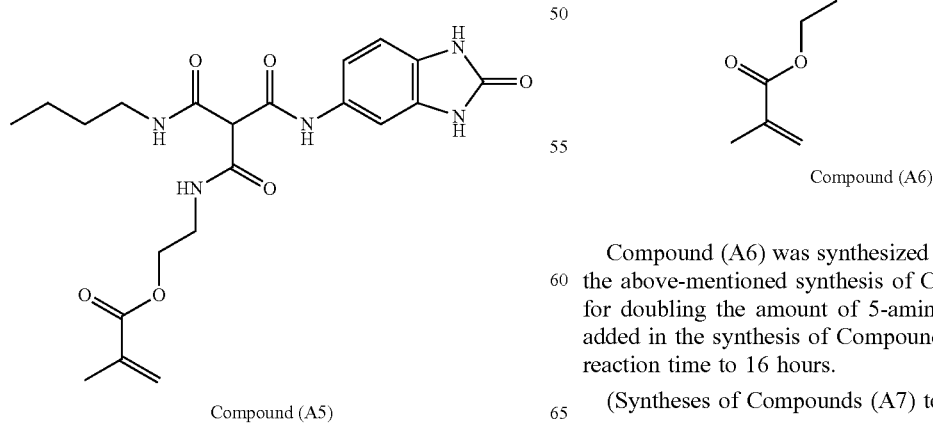

Compound (A6)

Compound (A6) was synthesized by the same method as the above-mentioned synthesis of Compound (A1), except for doubling the amount of 5-amino-2-benzimidazolinone added in the synthesis of Compound (A1) and altering the reaction time to 16 hours.

(Syntheses of Compounds (A7) to (A11))

The following Compounds (A7) to (A11) were synthesized by the same method as in the above.

Compound (A7)

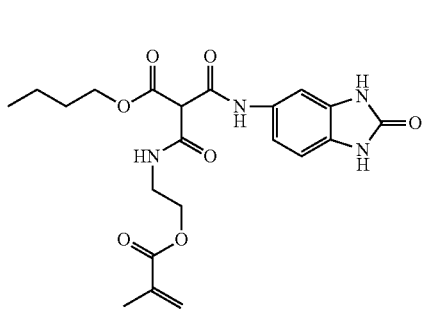

Compound (A8)

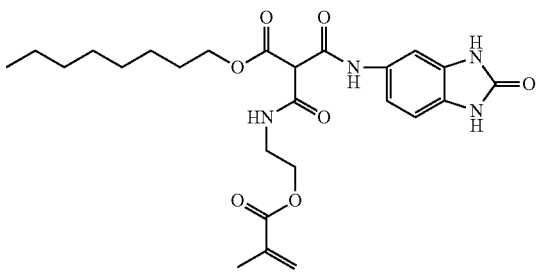

Compound (A9)

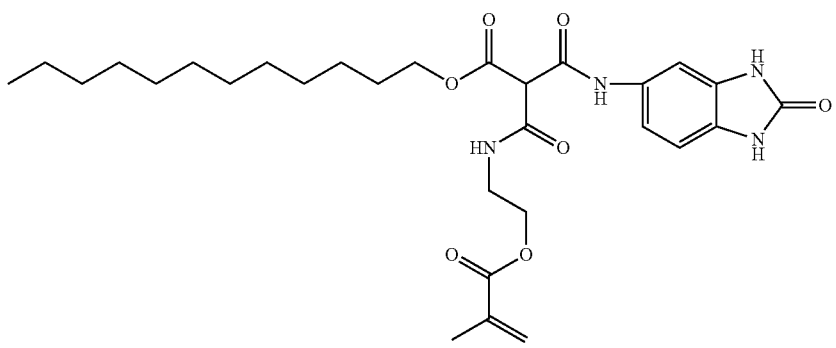

Compound (A10)

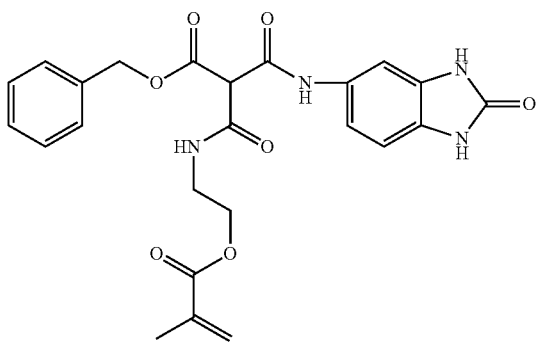

Compound (A11)

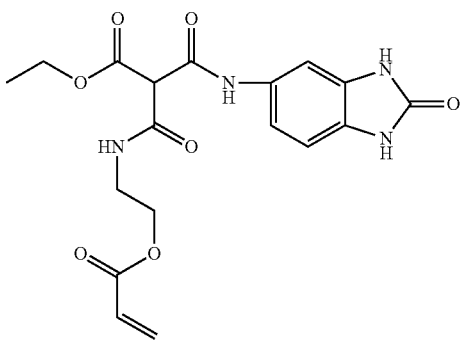

(Synthesis of Compound (A12))

Compound (A12) was synthesized according to the following scheme.

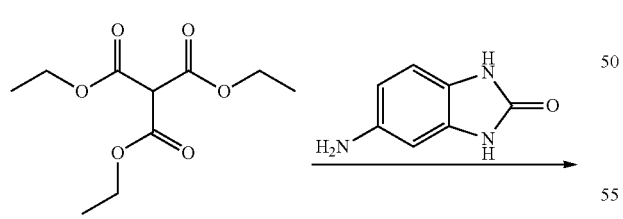

-continued

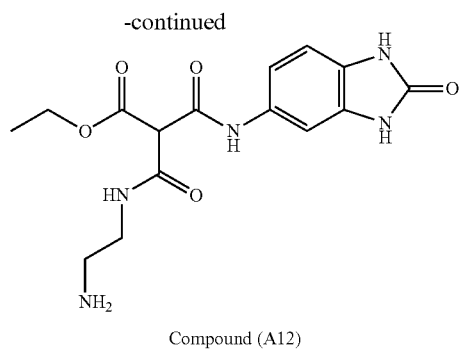

Compound (A12)

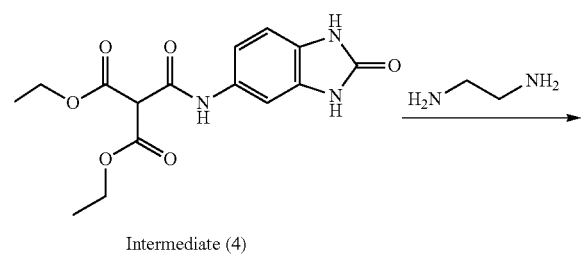

Intermediate (4)

An intermediate (4) was synthesized by the same method as the above-mentioned synthesis of the intermediate (2), except for altering 3-aminophenylureido to 5-amino-2-benzimidazolinone.

Compound (A12) was synthesized by the same method as the above-mentioned synthesis of Compound (A3), except for altering the intermediate (2) in the synthesis of Compound (A3) to the intermediate (4).

(Synthesis of Compound (A13))

Compound (A13) was synthesized according to the following scheme.

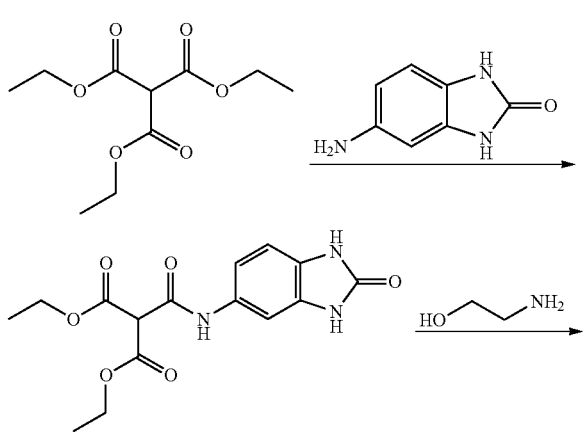

Intermediate (4)

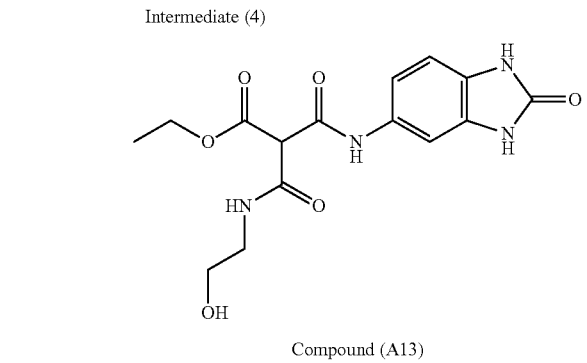

Compound (A13)

The intermediate (4) was synthesized by the same method as in Compound (A12)

Compound (A13) was synthesized by the same method as the synthesis of Compound (A3), except for altering the intermediate (2) in the synthesis of Compound (A3) to the intermediate (4), and ethylenediamine to 2-aminoethanol.

(Syntheses of Compounds (A14) and (A15))

The following Compounds (A14) and (A15) were synthesized by the same method as in the above.

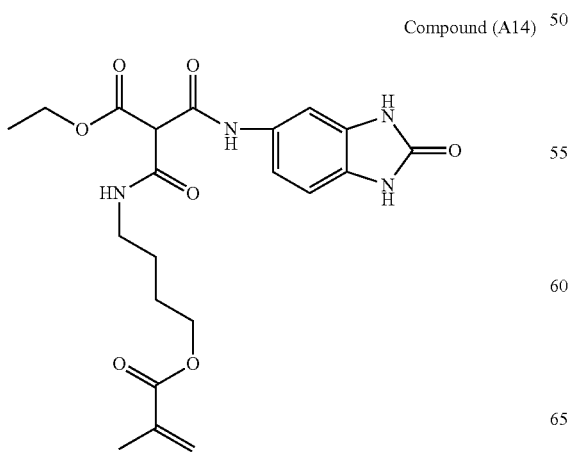

Compound (A14)

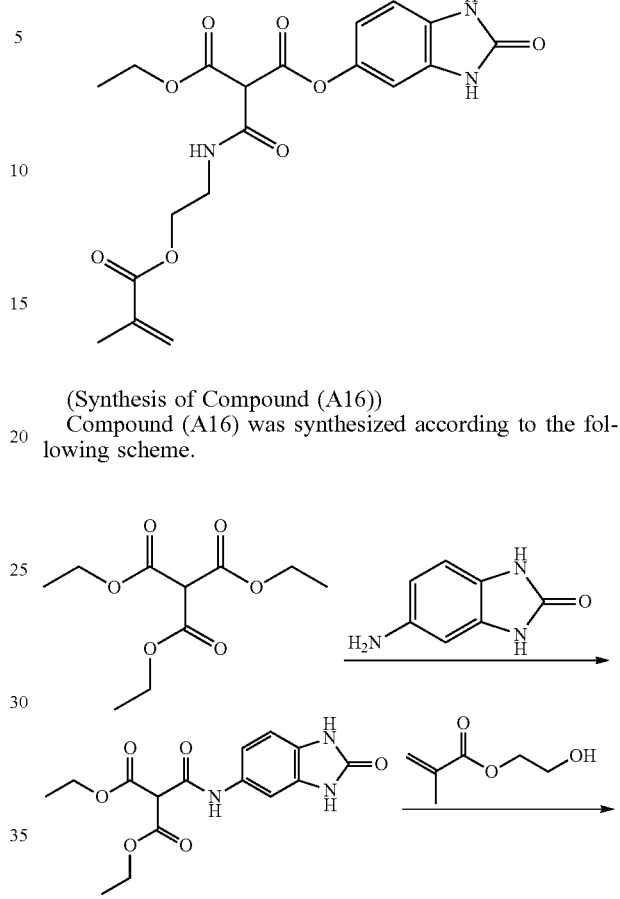

Compound (A15)

(Synthesis of Compound (A16))

Compound (A16) was synthesized according to the following scheme.

Intermediate (4)

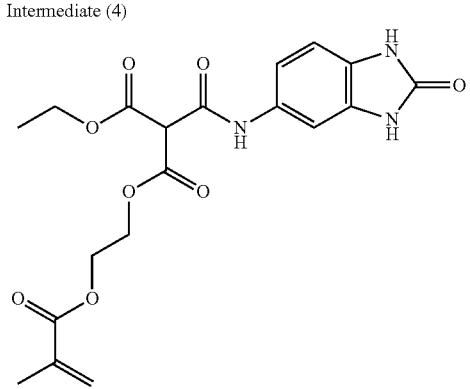

Compound (A16)

14.5 parts (62.4 mmol) of triethyl carboxymalonate, 11.4 parts (76.4 mmol) of 5-amino-2-benzimidazolinone and 0.138 part (0.626 mmol) of 2,6-di-tert-butyl-p-cresol were dissolved in 141 parts (1.93 mol) of N,N-dimethylformamide, and reacted under heating and stirring at 80° C. for 6 hours. After the reaction, N,N-dimethylformamide was distilled away under reduced pressure, and 300 parts (16.7 mol) of water was added to the obtained residue. The deposit was filtered to thereby obtain the intermediate (4).

18.8 parts (56.1 mmol) of the intermediate (4), 50.0 parts (0.684 mol) of N,N-dimethylformamide, 0.124 part (0.563 mmol) of 2,6-di-tert-butyl-p-cresol and 21.9 parts (0.168 mol) of 2-hydroxyethyl methacrylate were mixed, and reacted under heating and stirring at 80° C. for 10 hours. After the reaction, N,N-dimethylformamide was distilled away under reduced pressure, and 300 parts (16.7 mol) of water was added to the obtained residue. The deposit was filtered to thereby obtain Compound (A16).

(Synthesis of Compound (A17))

Compound (A17) was synthesized according to the following scheme.

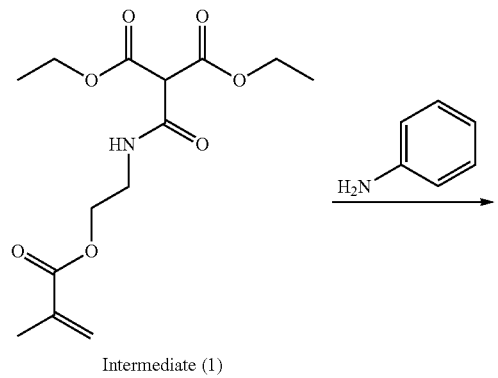

Intermediate (1)

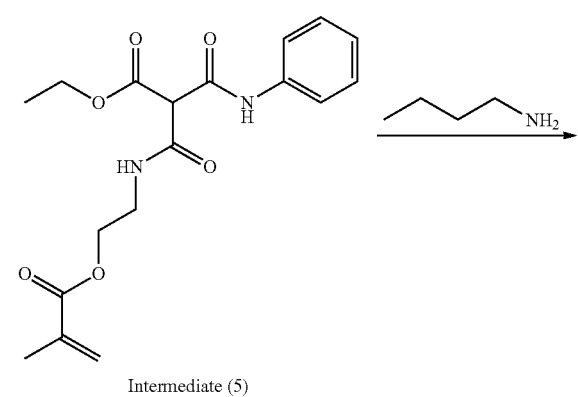

Intermediate (5)

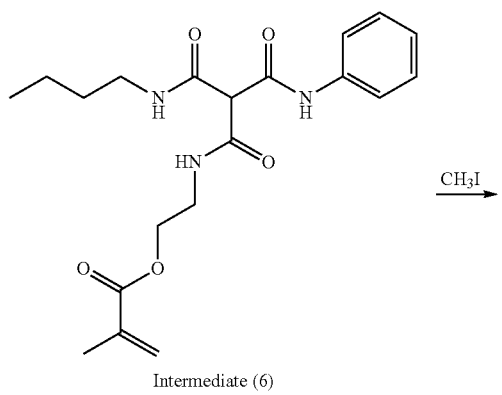

Intermediate (6)

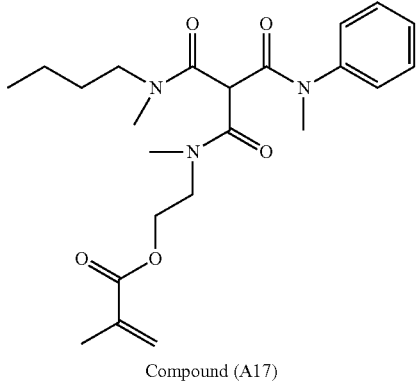

Compound (A17)

An intermediate (5) was synthesized by the same method as the above-mentioned synthesis of Compound (A1), except for altering 5-amino-2-benzimidazolinone in the synthesis of Compound (A1) to aniline. Further an intermediate (6) was obtained by the same method as the synthesis of Compound (A5), except for altering Compound (A1) in the synthesis of compound (A5) to the intermediate (5).

19.0 parts (48.8 mmol) of the intermediate (6) and 67.4 parts (0.488 mol) of potassium carbonate were dissolved in 141 parts (1.93 mol) of N,N-dimethylformamide, and 41.6 parts (0.293 mol) of iodomethane was dropwise added under ice cooling. Thereafter, the reaction liquid was heated to 60° C., and reacted under heating and stirring at 40° C. for 6 hours. After the reaction, N,N-dimethylformamide was distilled away under reduced pressure, and 200 parts (11.1 mol) of water and 200 parts (1.68 mol) of chloroform were added to the obtained residue and the resultant was separated to thereby extract a target material into the organic layer. The organic layer was washed with water and dried with magnesium sulfate, and thereafter concentrated to thereby obtain Compound (A17).

<Syntheses of Dispersants>

Then, by using the synthesized Compounds (A1) to (A17), Dispersants (D1) to (D37) to be used in the present invention, and Dispersants (D38) to (D44) to be used in Comparative Examples were synthesized.

(Synthesis of Dispersant (D1))

15.6 parts (0.150 mol) of styrene, 6.28 parts (15.0 mmol) of Compound (A1), 50.0 parts (0.684 mol) of N,N-dimethylformamide and 0.270 part (1.64 mmol) of azobisisobutyronitrile were put in an eggplant flask replaced by nitrogen, and stirred at 80° C. The polymerization was progressed while the molecular weight was being monitored by GPC, and when the molecular weight reached a desired value, the reaction was suspended by ice-water cooling to thereby obtain Dispersant (D1).

The obtained Dispersant (D1) was refined by solid-liquid separation in methanol being a poor solvent, and thereafter, the weight-average molecular weight was measured using NMR and GPC. Further the UV absorption at 480 nm was measured using a spectrophotometer, and the content a (parts by mole) of the unit A in terms of the molecular weight of Compound (A1) was calculated. Further the content b (parts by mole) of the unit B in terms of the molecular weight of styrene, and the value of a/(b+c) were calculated. The calculated results are shown in Table 2. Further the polymer type and the weight-average molecular weight (Mw) of the obtained Dispersant (D1) are shown in Table 2.

(Synthesis of Dispersant (D2))

6.28 parts (15.0 mmol) of Compound (A1), 50.0 parts (0.684 mol) of N,N-dimethylformamide and 0.270 part (1.64 mmol) of azobisisobutyronitrile were put in an eggplant flask replaced by nitrogen, and stirred at 80° C. The polymerization was progressed while the molecular weight was being monitored by NMR and GPC, and after it was ensured that 70% of Compound (A1) was consumed, 15.6 parts (0.150 mol) of styrene was added and further stirred at 80° C. The polymerization was progressed while the molecular weight was being monitored by GPC, and when the molecular weight reached a desired value, the reaction was suspended by ice-water cooling to thereby obtain Dispersant (D2).

The obtained Dispersant (D2) was refined by solid-liquid separation in methanol being a poor solvent, and the weight-average molecular weight was measured using NMR and GPC. Further the UV absorption at 480 nm of Dispersant (D2) was measured using a spectrophotometer, and the content a (parts by mole) in terms of the molecular weight of Compound (A1) was calculated. Further the content b (parts by mole) of the unit B in terms of the molecular weight of styrene, and the value of a/(b+c) were calculated. The calculated results are shown in Table 2. Further the polymer type and the weight-average molecular weight (Mw) of the obtained Dispersant (D2) are shown in Table 2.

(Syntheses of Dispersants (D3) to (D33) and (D38) to (D41))

Dispersants (D3) to (D33) and (D38) to (D41) were each synthesized by the same method as in Dispersant (D1) described above, except for suitably altering respective amounts of a compound having a partial structure of the formula (3), Compound B and Compound C of the kinds (names) shown in Table 2. The adsorption unit content a (parts by mole), the unit B content b (parts by mole), the unit C content c (parts by mole), the polymer type and the weight-average molecular weight (Mw) of the each synthesized Dispersant are shown in Table 2.

TABLE 2

Compositions of Synthesized Dispersants

| Dispersant | Compound Having Chemical Formula (3) Name | a (parts by mole) | Compound B Name | b (parts by mole) | Compound C Name | c (parts by mole) | a/(b + c) | Polymer Type | Mw |
|---|---|---|---|---|---|---|---|---|---|
| D1 | A(1) | 8 | styrene | 74 | — | 0 | 0.104 | random | 20,000 |
| D2 | A(1) | 7 | styrene | 70 | — | 0 | 0.100 | block | 19,000 |
| D3 | A(1) | 8 | vinyltoluene | 71 | — | 0 | 0.108 | random | 21,200 |
| D4 | A(1) | 6 | — | 0 | butyl methacrylate | 56 | 0.104 | random | 21,400 |
| D5 | A(1) | 8 | — | 0 | methyl acrylate | 75 | 0.105 | random | 19,800 |
| D6 | A(1) | 7 | styrene | 44 | butyl methacrylate | 23 | 0.110 | random | 19,300 |
| D7 | A(1) | 6 | styrene | 22 | butyl methacrylate | 38 | 0.105 | random | 19,600 |
| D8 | A(2) | 7 | styrene | 72 | — | 0 | 0.104 | random | 18,900 |
| D9 | A(4) | 8 | styrene | 81 | — | 0 | 0.104 | random | 19,900 |
| D10 | A(5) | 8 | styrene | 79 | — | 0 | 0.104 | random | 19,600 |
| D11 | A(6) | 8 | styrene | 74 | — | 0 | 0.104 | random | 20,200 |
| D12 | A(7) | 8 | styrene | 71 | — | 0 | 0.105 | random | 20,100 |
| D13 | A(8) | 7 | styrene | 69 | — | 0 | 0.100 | random | 20,100 |
| D14 | A(9) | 7 | styrene | 60 | — | 0 | 0.108 | random | 19,800 |
| D15 | A(10) | 8 | styrene | 78 | — | 0 | 0.104 | random | 20,700 |
| D16 | A(11) | 7 | styrene | 70 | — | 0 | 0.100 | random | 18,800 |
| D17 | A(14) | 7 | styrene | 64 | — | 0 | 0.105 | random | 20,100 |
| D18 | A(15) | 7 | styrene | 64 | — | 0 | 0.104 | random | 20,100 |
| D19 | A(16) | 7 | styrene | 68 | — | 0 | 0.104 | random | 20,500 |
| D20 | A(17) | 8 | styrene | 75 | — | 0 | 0.104 | random | 19,800 |
| D21 | A(1) | 1 | styrene | 137 | — | 0 | 0.004 | random | 26,400 |
| D22 | A(1) | 1 | styrene | 94 | — | 0 | 0.010 | random | 21,200 |
| D23 | A(1) | 2 | styrene | 91 | — | 0 | 0.023 | random | 21,200 |
| D24 | A(1) | 15 | styrene | 30 | — | 0 | 0.508 | random | 20,000 |
| D25 | A(1) | 19 | styrene | 18 | — | 0 | 1.053 | random | 20,700 |
| D26 | A(1) | 22 | styrene | 11 | — | 0 | 1.955 | random | 20,300 |
| D27 | A(1) | 23 | styrene | 8 | — | 0 | 2.813 | random | 20,500 |
| D28 | A(1) | 2 | styrene | 16 | — | 0 | 0.100 | random | 5,900 |
| D29 | A(1) | 3 | styrene | 30 | — | 0 | 0.106 | random | 9,800 |
| D30 | A(1) | 16 | styrene | 151 | — | 0 | 0.107 | random | 50,100 |
| D31 | A(1) | 34 | styrene | 323 | — | 0 | 0.106 | random | 107,000 |
| D32 | A(1) | 55 | styrene | 549 | — | 0 | 0.101 | random | 146,000 |
| D33 | A(1) | 68 | styrene | 669 | — | 0 | 0.102 | random | 199,000 |
| D38 | A(1) | 21 | — | 0 | — | 0 | — | homopolymer | 17,600 |
| D39 | — | 0 | styrene | 92 | — | 0 | 0.000 | homopolymer | 19,600 |
| D40 | — | 0 | — | 0 | butyl methacrylate | 77 | 0.000 | homopolymer | 20,200 |
| D41 | — | 0 | styrene | 69 | butyl methacrylate | 35 | 0.000 | random | 21,100 |

(Syntheses of Dispersants (D34) to (D37))
(Synthesis of Dispersant (D34))

65 parts of an adduct of 2.2 mol ethylene oxide to bisphenol A, 30 parts of dimethylterephthalic acid, 5 parts of trimellitic anhydride and 0.1 part of dibutyltin oxide were put in a 4-L glass four-necked flask. A thermometer, a stirring rod and a condenser were attached to the four-necked flask, which was then placed in a mantle heater. The mixture was gradually heated under stirring, and reacted at 200° C. for 6 hours to thereby obtain a polyester resin A. The acid value of the polyester resin A was 9 mgKOH/g, and the weight-average molecular weight thereof was 8,200.

Then, 30 parts of the fabricated polyester resin A was dissolved in 500 parts of dimethylformamide; 0.1 part of 4-N,N-dimethylaminopyridine and 0.7 part of phthalic anhydride were added, and reacted at room temperature for 3 hours to thereby obtain a polyester resin B having carboxylic acid groups on almost all terminals thereof. The acid value of the polyester resin B was 19 mgKOH/g.

20.0 parts (amount of COOH group: 6.77 mmol) of the polyester resin B (acid value: 19.0 mgKOH/g) was put in an eggplant flask replaced by nitrogen, and dissolved in 300 parts of N,N-dimethylformamide. The solution was cooled at 5° C. or lower; 1.61 parts (13.5 mmol) of thionyl chloride was slowly dropwise added; and after the dropping, the reaction liquid was heated to 600° C. After the reaction was carried out at 60° C. for 6 hours, excessive thionyl chloride was distilled away under reduced pressure to thereby obtain a polyester resin C liquid whose terminal carboxy groups had been acid-chlorinated.

2.85 parts (8.11 mmol) of Compound (A3) was dissolved in 20 parts of N,N-dimethylformamide to thereby prepare a Compound (A3) liquid. The Compound (A3) liquid was slowly dropwise added at 5° C. or lower to the above polyester resin C liquid; and after the dropping, the reaction was carried out at 60° C. for 2 hours. After the reaction, the solvent was distilled away under reduced pressure, and the resultant was washed with methanol, and dried to thereby obtain Dispersant (D34) in which Compound (A3) was added to terminals of the polyester resin. The acid value of the Dispersant was 0, and the weight-average molecular weight thereof was 8,800. The polymer type and the weight-average molecular weight (Mw) of the obtained Dispersant (D34) are shown in Table 3.

(Synthesis of Dispersant (D35))

156 parts (1.50 mol) of styrene, 5.69 parts (79.0 mmol) of acrylic acid, 500 parts (6.84 mol) of N,N-dimethylformamide and 2.70 parts (16.4 mmol) of azobisisobutyronitrile were put in an eggplant flask replaced by nitrogen. The reaction liquid was heated to 80° C., and the polymerization was progressed while the molecular weight was being monitored by GPC; and when the molecular weight reached a desired value, the reaction was suspended by ice-water cooling. The reaction liquid was refined by a dialysis method to thereby obtain a styrene-acrylic acid polymer having an acid value of 27.4 mgKOH/g and a weight-average molecular weight of 20,500.

Carboxy groups of the styrene-acrylic acid polymer were acid-chlorinated by the same method as in the above-mentioned synthesis of Dispersant (D34), and reacted with Compound (A12) to thereby obtain Dispersant (D35). The acid value of the Dispersant (D35) was 0, and the weight-average molecular weight thereof was 22,200. As a result of the compositional analysis of the obtained Dispersant (D35), the a/(b+c) value was 0.053. Additionally, the polymer type and the weight-average molecular weight (Mw) are shown in Table 3.

(Synthesis of Dispersant (D36))

Dispersant (D36) was synthesized by the same method as in the above-mentioned synthesis of Dispersant (D34), except for altering Compound (A3) to Compound (A13). The weight-average molecular weight of the Dispersant (D36) was 9,000. The polymer type and the weight-average molecular weight (Mw) of the obtained Dispersant (D36) are shown in Table 3.

(Synthesis of Dispersant (D37))

66.1 parts of an adduct of 2.2 mol propylene oxide to bisphenol A, 33.9 parts of dimethylterephthalic acid, 5 parts of trimellitic anhydride and 2 parts of potassium titanyl oxalate were put in a four-necked flask. A thermometer, a stirring rod and a condenser were attached to the four-necked flask, which was then placed in a mantle heater. The mixture was gradually heated under stirring, and reacted at 200° C. for 6 hours to thereby obtain a polyester resin D. The weight-average molecular weight of the polyester resin D was 7,700.

100 parts of xylene was put in an eggplant flask replaced by nitrogen, and 60 parts of the polyester resin D was dissolved in a nitrogen flow under stirring at 50° C. 35 parts of styrene, 5 parts of Compound (A1) and 1.5 parts of t-butylperoxyisopropyl monocarbonate (Perbutyl I, manufactured by NOF Corp.) were mixed in another vessel, and dropwise added to the eggplant flask; the internal temperature was raised to 125° C., and the mixture was stirred for 4 hours and then cooled to room temperature. Thereafter, the solvent was distilled away under reduced pressure; and the resultant was washed with methanol, and dried to thereby obtain Dispersant (D37) being a polyester/styrene graft composite polymer. The weight-average molecular weight of the Dispersant (D37) was 23,500. The polymer type and the weight-average molecular weight (Mw) of the obtained Dispersant (D37) are shown in Table 3.

TABLE 3

Compositions of Synthesized Dispersants

| Dispersant | Compound Having Partial Structure of Chemical Formula (3) | Raw Material Polymer | Polymer Type | Mw |
|---|---|---|---|---|
| D34 | A(3) | PES1 | polyester | 8,800 |
| D35 | A(12) | St/AA | styrene/acryl (random) | 22,200 |
| D36 | A(13) | PES1 | polyester | 9,000 |
| D37 | A(1) | — | polyester/styrene graft composite polymer | 23,500 |

(Synthesis of Dispersant (D42))
[Synthesis of Compound X]

Compound X represented by the following formula (X) was synthesized by reference to the description of a synthesis example 1 in Japanese Patent Application Laid-Open No. 2003-081948.

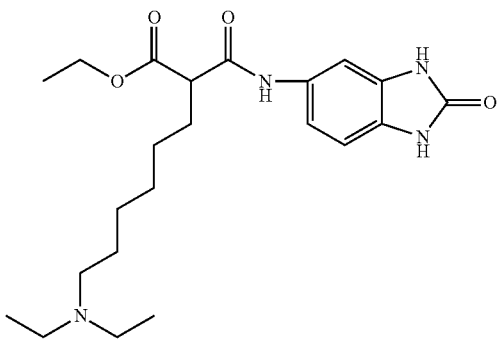

(X)

[Synthesis of a Styrene-Acrylic Acid Polymer]

156 parts (1.50 mol) of styrene, 32.4 parts (0.450 mol) of acrylic acid, 500 parts (6.84 mol) of N,N-dimethylformamide, and 2.70 parts (16.4 mmol) of azobisisobutyronitrile were put in an eggplant flask replaced by nitrogen, and stirred at 80° C. The polymerization was progressed while the molecular weight was being monitored by GPC; and when the molecular weight reached a desired value, the reaction was suspended by ice-water cooling to thereby obtain a styrene-acrylic acid polymer. The styrene-acrylic acid polymer was refined by a dialysis method. The weight-average molecular weight of the styrene-acrylic acid polymer as measured using NMR and GPC was 20,600.

[Preparation of Dispersant (D42)]

0.213 part (0.509 mmol) of the obtained Compound X, 103 parts (5.00 mmol) of the styrene-acrylic acid polymer and 40 parts of a tetrahydrofuran-methanol mixed liquid (1:1 in volume ratio) were mixed in a roll mill. After the mixing, the solvent was removed to thereby obtain Dispersant (D42). The value of x/(b+c) was 0.102, where x (parts by mole) represents an amount of the Compound X; b (parts by mole) represents a content of the unit B in the styrene-acrylic acid polymer; and c (parts by mole) represents a content of the unit C therein.

(Synthesis of Dispersant (D43))

[Synthesis of Compound Y]

Compound Y represented by the following formula (Y) was synthesized by reference to the description of a synthesis example 1 in Japanese Patent Application Laid-Open No. 2003-238837.

(Y)

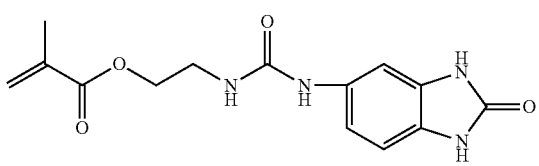

[Synthesis of Dispersant (D43)]

15.6 parts (0.150 mol) of styrene, 4.56 parts (15.0 mmol) of the Compound Y, 50.0 parts (0.684 mol) of N,N-dimethylformamide and 0.270 part (1.64 mmol) of azobisisobutyronitrile were put in an eggplant flask replaced by nitrogen, and stirred at 80° C. The polymerization was progressed while the molecular weight was being monitored by GPC; and when the molecular weight reached a desired value, the reaction was suspended by ice-water cooling to thereby obtain Dispersant (D43).

The obtained Dispersant (D43) was refined by solid-liquid separation in methanol being a poor solvent, and thereafter, the weight-average molecular weight was measured using NMR and GPC. Further the UV absorption at 480 nm was measured using a spectrophotometer, and the content y (parts by mole) of the unit Y in terms of the molecular weight of the Compound Y was calculated. Further the content b (parts by mole) of the unit B in terms of the molecular weight of styrene, and the value of y/(b+c) were calculated. The calculated results are shown in Table 4. Further the polymer type and the weight-average molecular weight (Mw) of the obtained Dispersant (D43) are shown in Table 4.

(Synthesis of Dispersant (D44))

[Synthesis of Compound Z]

Compound Z represented by the following formula (Z) was synthesized by reference to the description in Japanese Patent Application Laid-Open No. 2009-501253.

(Z)

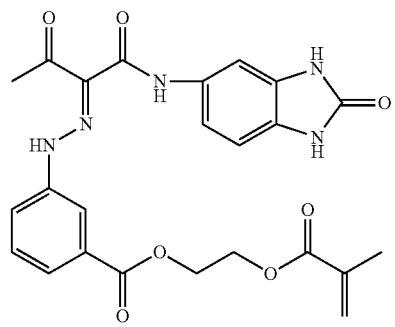

[Synthesis of Dispersant (D44)]

15.6 parts (0.150 mol) of styrene, 7.40 parts (15.0 mmol) of the Compound Z, 50.0 parts (0.684 mol) of N,N-dimethylformamide, and 0.270 part (1.64 mmol) of azobisisobutyronitrile were put in an eggplant flask replaced by nitrogen, and stirred at 80° C. The polymerization was progressed while the molecular weight was being monitored by GPC; and when the molecular weight reached a desired value, the reaction was suspended by ice-water cooling to thereby obtain Dispersant (D44).

The obtained Dispersant (D44) was refined by solid-liquid separation in methanol being a poor solvent, and the weight-average molecular weight was measured using NMR and GPC. Further the UV absorption at 380 nm was measured using a spectrophotometer, and the content z (parts by mole) of the unit Z in terms of the molecular weight of the Compound Z was calculated. Further the content b (parts by mole) of the unit B in terms of the molecular weight of styrene, and the value of z/(b+c) were calculated. The calculated results are shown in Table 4. Further the polymer type and the weight-average molecular weight (Mw) of the obtained Dispersant (D44) are shown in Table 4.

TABLE 4

Compositions of Synthesized Dispersants

| Dispersant | Compound Having Chemical Formula (3) Name | a | Y y | Z z | Compound B Name | b | Compound C Name | c | y/(b + c) | z/(b + c) | Polymer Type | Mw |
|---|---|---|---|---|---|---|---|---|---|---|---|---|
| D42 | — | — | Compound X + styrene-acrylic acid polymer | | | | | | — | — | random | 20,600 |
| D43 | — | — | 8 | — | styrene | 75 | — | — | 0.107 | — | random | 20,500 |
| D44 | — | — | — | 7 | styrene | 64 | — | — | — | 0.103 | random | 19,500 |

Hereinafter, three Production Examples of black toner particles will be described.

<Production Example 1 of a Toner Particle>
[Preparation Step of a Colorant Dispersion Liquid 1]
Styrene: 100.0 parts
Carbon black (CB): 20.0 parts, Nipex35 (manufactured by Orion Engineered Carbons Inc.)
Dispersant D1: 4.0 parts The above materials were introduced to an attritor (manufactured by Mitsui Mining Co., Ltd.), and stirred at 200 rpm at 25° C. for 180 min by using zirconia beads (200 parts) of 2.5 mm in radius to thereby prepare a colorant dispersion liquid 1.

[Preparation Step of a Toner Composition Solution]
The colorant dispersion liquid 1: 40.0 parts
Styrene: 33.5 parts
n-Butyl acrylate: 24.5 parts
Paraffin wax: 10.0 parts, (HNP-9, manufactured by Nippon Seiro Co., Ltd., melting point: 75° C.)

The above materials were mixed and heated at 65° C., and the resultant mixture was homogeneously dissolved and dispersed at 5,000 rpm for 60 min by using a T.K. homomixer (manufactured by Tokushu Kika Kogyo Co., Ltd.) to thereby obtain a toner composition solution 1.

[Preparation Step of a Toner Particle Dispersion Liquid]
450 parts of a 0.1M $Na_3PO_4$ aqueous solution was added to 710 parts of ion-exchange water in a 2-L four-necked flask equipped with a T.K. homomixer, and heated at 60° C.; and thereafter, 67.7 parts of a 1.0M $CaCl_2$ aqueous solution was gradually added to thereby obtain an aqueous medium containing calcium phosphate. 1.4 parts of sodium dodecylbenzenesulfonate was dissolved in the obtained aqueous medium. Then, 8 parts of a 70% toluene solution of a polymerization initiator, 1,1,3,3-tetramethylbutyl peroxy-2-ethylhexanoate, was dissolved in the toner composition solution 1, and fully mixed, and thereafter the resultant mixture was added to the above aqueous medium. The resultant was stirred at a temperature of 62° C. in a nitrogen atmosphere at 12,000 rpm for 10 min to granulate the polymerizable monomer composition. Thereafter, the resultant was heated at 75° C. under stirring by a paddle stirring blade and subjected to polymerization for 7.5 hours, and the polymerization reaction was terminated. Then, the residual monomer was distilled away under reduced pressure, and the aqueous medium was cooled to thereby obtain a toner particle dispersion liquid.

Hydrochloric acid was added to the toner particle dispersion liquid to make the pH to be 1.4, and the dispersion liquid was stirred for 1 hour to thereby dissolve calcium phosphate. The resultant was subjected to solid-liquid separation using a pressure filter to thereby obtain a toner cake. The resultant was 5 times repeatedly subjected to washing operation using ion-exchange water, and thereafter dried to thereby obtain a black toner particle.

<Production Example 2 of a Toner Particle>
[Preparation Step of a Colorant Dispersion Liquid 2]
Toluene: 350.0 parts
Carbon black (CB): 56.0 parts, Nipex35 (manufactured by Orion Engineered Carbons Inc.)
Dispersant D1: 11.2 parts The above materials were introduced to an attritor (manufactured by Mitsui Mining Co., Ltd.), and stirred at 200 rpm at 25° C. for 180 min by using zirconia beads (200 parts) of 2.5 mm in radius to thereby prepare a colorant dispersion liquid 2.

[Preparation Step of a Toner Composition Solution 2]
The colorant dispersion liquid 2: 250.0 parts
Styrene acryl resin: 490.0 parts (a copolymer of styrene: n-butyl acrylate=75:25 (mass ratio)) (Mw=28,000, Tg=57° C.)
Paraffin wax: 50.0 parts (HNP-9, manufactured by Nippon Seiro Co., Ltd., melting point: 75° C.)

The above materials were mixed and heated at 65° C., and homogeneously dispersed at 5,000 rpm for 60 min by using a T.K. homomixer (manufactured by Tokushu Kika Kogyo Co., Ltd.) to thereby obtain a toner composition solution 2.

[Preparation Step of a Toner Particle Dispersion Liquid 2]
300 parts of a 0.5M $Na_3PO_4$ aqueous solution was added to 1,200 parts of ion-exchange water in a 2-L four-necked flask equipped with a T.K. homomixer. Thereafter, the stirring was regulated at 12,000 rpm and the solution was heated at 6° C. Thereafter, 25.7 parts of a 1.0M $CaCl_2$ aqueous solution was gradually added to thereby obtain an aqueous medium containing calcium phosphate. 1.0 part of sodium dodecylbenzenesulfonate was dissolved in the obtained aqueous medium.

Then, the toner composition solution 2 was added to the aqueous medium. The resultant was stirred at a temperature of 65° C. in a nitrogen atmosphere at 12,000 rpm for 30 min to granulate particles of the toner composition solution 2. Then, toluene was distilled away under reduced pressure, and the aqueous medium was cooled to thereby obtain a toner particle dispersion liquid 2.

Hydrochloric acid was added to the toner particle dispersion liquid to make the pH to be 1.4, and the dispersion liquid was stirred for 1 hour to thereby dissolve calcium phosphate. The resultant was subjected to solid-liquid separation using a pressure filter to thereby obtain a toner cake. Then, the resultant was 5 times repeatedly subjected to washing operation using ion-exchange water, and thereafter dried to thereby obtain a black toner particle.

<Production Example 3 of a Toner Particle>
Styrene acryl resin: 98.0 parts (a copolymer of styrene: n-butyl acrylate=75:25 (mass ratio)) (Mw=28,000, Tg=57° C.)

Carbon black (CB): 8.0 parts, Nipex35 (manufactured by Orion Engineered Carbons Inc.)
Paraffin wax: 10.0 parts, (HNP-9, manufactured by Nippon Seiro Co., Ltd., melting point: 75° C.)
Dispersant D1: 1.6 parts The materials in the above formulation were well mixed by an FM mixer (manufactured by Nippon Coke & Engineering Co., Ltd.), and thereafter kneaded by a twin-screw kneader set at a temperature of 130° C. The obtained kneaded material was cooled, and coarsely crushed into 2 mm or smaller by a hammer mill to thereby obtain a coarse crushed material. The obtained coarse crushed material was finely ground by using a mechanical grinding machine (manufactured by Turbo Kogyo Co., Ltd., type: TurboMill T250-RS). Thereafter, the obtained finely ground material was classified using a multi-division classifier utilizing the Coanda effect to thereby obtain a black toner particle.

Then, a Production Example of a magenta toner particles will be described.

<Production Example 4 of a Toner Particle>
[Preparation Step of a Colorant Dispersion Liquid 3]
Styrene: 100.0 parts
C.I. Pigment Red 122 (PR-122): 16.7 parts, (Toner Magenta E, manufactured by Clariant International Ltd.)
Dispersant D1: 3.33 parts The above materials were introduced to an attritor (manufactured by Mitsui Mining Co., Ltd.), and stirred at 200 rpm at 25° C. for 180 min by using zirconia beads (200 parts) of 2.5 mm in radius to thereby prepare a colorant dispersion liquid 3.

[Preparation Step of a Toner Composition Solution 3]
The colorant dispersion liquid 3: 53.9 parts
Styrene: 19.6 parts
n-Butyl acrylate: 24.5 parts
Paraffin wax: 10.0 parts, (HNP-9, manufactured by Nippon Seiro Co., Ltd., melting point: 75° C.)

The above materials were mixed and heated at 65° C., and homogeneously dissolved and dispersed at 5,000 rpm for 60 min by using a T.K. homomixer (manufactured by Tokushu Kika Kogyo Co., Ltd.) to thereby obtain a toner composition solution 3. Thereafter, a magenta toner particle was obtained as in the toner particle Production Example 1.

Then, a Production Example of a cyan toner particle will be described.

<Production Example 5 of a Toner Particle>
[Preparation Step of a Colorant Dispersion Liquid 4]
Styrene: 100.0 parts
C.I. Pigment Blue 15:3: 16.7 parts
Dispersant D1: 3.33 parts The above materials were introduced to an attritor (manufactured by Mitsui Mining Co., Ltd.), and stirred at 200 rpm at 25° C. for 180 min by using zirconia beads (200 parts) of 2.5 mm in radius to thereby prepare a colorant dispersion liquid 4.

[Preparation Step of a Toner Composition Solution 4]
The colorant dispersion liquid 4: 53.9 parts
Styrene: 19.6 parts
n-Butyl acrylate: 24.5 parts
Paraffin wax: 10.0 parts, (HNP-9, manufactured by Nippon Seiro Co., Ltd., melting point: 75° C.)

The above materials were mixed and heated at 65° C., and homogeneously dissolved and dispersed at 5,000 rpm for 60 min by using a T.K. homomixer (manufactured by Tokushu Kika Kogyo Co., Ltd.) to thereby obtain a toner composition solution 4. Thereafter, a cyan toner particle was obtained as in the toner particle Production Example 1. Hereinafter, a Production Example of a yellow toner particle will be described.

<Production Example 6 of a Toner Particle>
[Preparation Step of a Colorant Dispersion Liquid 5]
Styrene: 100.0 parts
C.I. Pigment Yellow 155 (PY-155): 16.7 parts, (Peliotol Yellow D1155, manufactured by BASF)
Dispersant D1: 3.33 parts The above materials were introduced to an attritor (manufactured by Mitsui Mining Co., Ltd.), and stirred at 200 rpm at 25° C. for 180 min by using zirconia beads (200 parts) of 2.5 mm in radius to thereby prepare a colorant dispersion liquid 5.

[Preparation Step of a Toner Composition Solution 5]
The colorant dispersion liquid 5: 53.9 parts
Styrene: 19.6 parts
n-Butyl acrylate: 24.5 parts
Paraffin wax: 10.0 parts, (HNP-9, manufactured by Nippon Seiro Co., Ltd., melting point: 75° C.)

The above materials were mixed and heated at 65° C., and homogeneously dispersed at 5,000 rpm for 60 min by using a T.K. homomixer (manufactured by Tokushu Kika Kogyo Co., Ltd.) to thereby obtain a toner composition solution 5. Thereafter, a yellow toner particle was obtained as in the toner particle Production Example 1.

The formulations and the physical properties of the obtained toner particles are shown in Table 5.

TABLE 5

| Toner Particle | Production Method | Pigment Kind | Dispersant Kind | Particle Diameter D4(μm) |
|---|---|---|---|---|
| Toner Particle 1 | Production Example 1 | CB | D1 | 6.7 |
| Toner Particle 2 | Production Example 2 | CB | D1 | 6.8 |
| Toner Particle 3 | Production Example 3 | CB | D1 | 6.4 |
| Toner Particle 4 | Production Example 4 | Pig1 | D1 | 6.4 |
| Toner Particle 5 | Production Example 5 | Pig2 | D1 | 6.7 |
| Toner Particle 6 | Production Example 6 | Pig3 | D1 | 6.8 |
| Toner Particle 7 | Production Example 4 | Pig1 | D2 | 6.9 |
| Toner Particle 8 | Production Example 4 | Pig1 | D3 | 7.0 |
| Toner Particle 9 | Production Example 4 | Pig1 | D4 | 6.9 |
| Toner Particle 10 | Production Example 4 | Pig1 | D5 | 7.1 |
| Toner Particle 11 | Production Example 4 | Pig1 | D6 | 6.9 |
| Toner Particle 12 | Production Example 4 | Pig1 | D7 | 6.9 |
| Toner Particle 13 | Production Example 4 | Pig1 | D8 | 7.2 |
| Toner Particle 14 | Production Example 4 | Pig1 | D9 | 7.0 |
| Toner Particle 15 | Production Example 4 | Pig1 | D10 | 6.8 |
| Toner Particle 16 | Production Example 4 | Pig1 | D11 | 6.7 |
| Toner Particle 17 | Production Example 4 | Pig1 | D12 | 6.8 |
| Toner Particle 18 | Production Example 4 | Pig1 | D13 | 6.8 |
| Toner Particle 19 | Production Example 4 | Pig1 | D14 | 6.9 |
| Toner Particle 20 | Production Example 4 | Pig1 | D15 | 7.0 |
| Toner Particle 21 | Production Example 4 | Pig1 | D16 | 7.1 |
| Toner Particle 22 | Production Example 4 | Pig1 | D17 | 7.2 |
| Toner Particle 23 | Production Example 4 | Pig1 | D18 | 6.8 |
| Toner Particle 24 | Production Example 4 | Pig1 | D19 | 6.9 |
| Toner Particle 25 | Production Example 4 | Pig1 | D20 | 6.7 |
| Toner Particle 26 | Production Example 4 | Pig1 | D21 | 6.6 |
| Toner Particle 27 | Production Example 4 | Pig1 | D22 | 6.8 |
| Toner Particle 28 | Production Example 4 | Pig1 | D23 | 6.9 |
| Toner Particle 29 | Production Example 4 | Pig1 | D24 | 7.0 |
| Toner Particle 30 | Production Example 4 | Pig1 | D25 | 6.8 |
| Toner Particle 31 | Production Example 4 | Pig1 | D26 | 6.9 |
| Toner Particle 32 | Production Example 4 | Pig1 | D27 | 6.9 |
| Toner Particle 33 | Production Example 4 | Pig1 | D28 | 7.1 |
| Toner Particle 34 | Production Example 4 | Pig1 | D29 | 7.0 |
| Toner Particle 35 | Production Example 4 | Pig1 | D30 | 7.0 |
| Toner Particle 36 | Production Example 4 | Pig1 | D31 | 6.8 |
| Toner Particle 37 | Production Example 4 | Pig1 | D32 | 6.7 |
| Toner Particle 38 | Production Example 4 | Pig1 | D33 | 6.9 |

TABLE 5-continued

| Toner Particle | Production Method | Pigment Kind | Dispersant Kind | Particle Diameter D4(μm) |
|---|---|---|---|---|
| Toner Particle 39 | Production Example 4 | Pig1 | D34 | 6.8 |
| Toner Particle 40 | Production Example 4 | Pig1 | D35 | 7.0 |
| Toner Particle 41 | Production Example 4 | Pig1 | D36 | 7.1 |
| Toner Particle 42 | Production Example 4 | Pig1 | D37 | 6.9 |
| Toner Particle 43 | Production Example 4 | Pig1 | D38 | 7.3 |
| Toner Particle 44 | Production Example 4 | Pig1 | D39 | 6.8 |
| Toner Particle 45 | Production Example 4 | Pig1 | D40 | 7.1 |
| Toner Particle 46 | Production Example 4 | Pig1 | D41 | 6.8 |
| Toner Particle 47 | Production Example 4 | Pig1 | D42 | 6.8 |
| Toner Particle 48 | Production Example 4 | Pig1 | D43 | 7.0 |
| Toner Particle 49 | Production Example 4 | Pig1 | D44 | 7.0 |

CB: carbon black
Pig1: C.I. Pigment Red 122
Pig2: C.I. Pigment Blue 15:3
Pig3: C.I. Pigment Yellow 155

<Production Example of Toners>

100.0 parts of the obtained toner particles 1 to 49 each and 1.5 parts of a hydrophobic silica micropowder were mixed by a Mitsui Henschel mixer (manufactured by Mitsui Miike Chemical Engineering Machinery, Co., Ltd.) for 300 sec to thereby obtain Toners 1 to 49. Here, the used silica micropowder was a hydrophobic silica micropowder having been surface-treated with hexamethyldisilazane, and had a number-average particle diameter (D1) of the primary particle of 10 nm.

<Evaluations of the Compounds, the Dispersants and the Toners>

The evaluations of the obtained Compounds, Dispersants and Toners were carried out as follows.

(Evaluation of the Compounds)

[Adsorbability to the Coloring Materials]

0.2 part of the each Compound was dissolved in 20 parts of N,N-dimethylformamide to thereby prepare a solution (O). 1 part of carbon black as the coloring material was added to 10 parts of the solution (O), and ultrasonically dispersed for 30 min. After the solution was allowed to stand still at room temperature for 1 hour, the solution was centrifugally separated to recover a supernatant liquid. N,N-dimethylformamide was added to each of the solution (0) and the supernatant liquid, so that they were diluted to the same dilution magnification for each sample; and the absorbances at a wavelength of 380 nm for Compound Z and at that of 480 nm for the other were measured. Then, the adsorptivity rate was calculated from the following formula (9), and the adsorbability of each Compound to the coloring material was evaluated according to the following evaluation criteria. The results are shown in Table 6.

$$\text{An adsorptivity rate (\%)} = (1 - P/Q) \times 100 \quad (9)$$

P: the absorbance of a diluted liquid of the supernatant liquid
Q: the absorbance of a diluted liquid of the solution (0)

[Evaluation Criteria]
A: the adsorptivity rate was 95% or higher
B: the adsorptivity rate was 90% or higher and lower than 95%
C: the adsorptivity rate was lower than 90%

[Coloring Property]

N,N-dimethylformamide was added to the solution (O), which was thus diluted to 1,000 times, and the absorbances at 300 nm to 700 nm were measured. The coloring property was evaluated according to the following criteria from a maximum absorbance in the measurement range. The results are shown in Table 6.

[Evaluation Criteria]
A: The maximum absorbance was lower than 0.010
B: The maximum absorbance was 0.010 or higher

TABLE 6

Evaluation Results of the Compounds

| | Adsorbability | Coloring Property |
|---|---|---|
| Compound A1 | A | A |
| Compound A2 | B | A |
| Compound A3 | B | A |
| Compound A4 | A | A |
| Compound A5 | A | A |
| Compound A6 | A | A |
| Compound A7 | A | A |
| Compound A8 | A | A |
| Compound A9 | A | A |
| Compound A10 | A | A |
| Compound A11 | A | A |
| Compound A12 | A | A |
| Compound A13 | A | A |
| Compound A14 | A | A |
| Compound A15 | A | A |
| Compound A16 | A | A |
| Compound A17 | B | A |
| Compound X | C | A |
| Compound Y | C | A |
| Compound Z | B | B |

As is clear from the results shown in Table 6, Compounds (A1) to (A17) were compounds excellent in the adsorbability and reduced in the coloring property of the Compounds themselves.

(Evaluations of the Dispersants)

[Solubility to the Media]

0.25 part of the each Dispersant was added to 20 parts of a medium for evaluation, and the solubility of the Dispersant was evaluated according to the following evaluation criteria. The kinds of the media used for evaluation and the results are shown in Table 7.

[Evaluation Criteria]
A: being easily soluble (being dissolved by hand shaking mixing)
B: being soluble (being dissolved by stirring)
C: being soluble (being dissolved by means of ultrasonic waves, heating or the like)
D: insoluble matter remaining

[Adsorbability to the Coloring Materials]

0.25 part of each Dispersant was dissolved in 20 parts of a medium for evaluation to thereby prepare a solution (S) of the each Dispersant. 1 part of a coloring material concerned was added to 10 parts of the solution (S), and ultrasonically dispersed for 30 min. The resultant was allowed to stand still at room temperature for 1 hour, and centrifugally separated to recover a supernatant liquid. The medium for evaluation was added to each of the solution (S) and the supernatant liquid, which were thus diluted to the same dilution magnification for each sample; and the absorbances at a wavelength of 280 nm for Dispersants (D39) to (D41), at that of 380 nm for Dispersant (D44) and at that of 480 nm for the other were measured. Then, the adsorptivity rate was calculated from the following formula (10), and the adsorbability of each Compound to the coloring material was evaluated according to the following evaluation criteria. The results are shown in Table 7.

$$\text{An adsorptivity rate (\%)} = (1 - T/U) \times 100 \quad (10)$$

T: the absorbance of a diluted liquid of the supernatant liquid
U: the absorbance of a diluted liquid of the solution (S)
[Evaluation Criteria]
A: the adsorptivity rate was 95% or higher
B: the adsorptivity rate was 90% or higher and lower than 95%
C: the adsorptivity rate was 80% or higher and lower than 90%
D: the adsorptivity rate was lower than 80%

[Coloring Material Dispersibility]

0.25 part of the each Dispersant was dissolved in 20 parts of a medium for evaluation to thereby prepare a solution (V) of the each Dispersant. 1 part of a coloring material concerned was added to 10 parts of the solution (V), and ultrasonically dispersed for 30 min, and thereafter allowed to stand still at room temperature for 1 hour to thereby obtain a coloring material dispersion. The obtained coloring material dispersion was placed in a closed state, and subjected to a preservation test at 60° C. for two-week preservation. Further the volume-average particle diameters before and after the preservation test of the coloring material were measured using a particle size analyzer (trade name: "Micro Track UPA-EX250", manufactured by Nikkiso Co., Ltd.). Then, the particle diameter increase rate was calculated by the following formula (11), and the coloring material dispersibility of the Dispersants was evaluated according to the following evaluation criteria. The results are shown in Table 7.

A particle diameter increase rate (%)=(a particle diameter after the test−a particle diameter before the test)/(the particle diameter before the test)×100     (11)

[Evaluation Criteria]
A: the particle diameter increase rate (%) was lower than 10%
B: the particle diameter increase rate (%) was 10% or higher and lower than 20%
C: the particle diameter increase rate (%) was 20% or higher and lower than 50%
D: the particle diameter increase rate (%) was 50% or higher

TABLE 7

Evaluation Results of the Dispersants

| | | Dispersant | Medium for Evaluation | Coloring Material | Solubility | Adsorbability to Coloring Material | Coloring Material Dispersibility |
|---|---|---|---|---|---|---|---|
| Examples | 1 | D1 | toluene | CB | A | A | A |
| | 2 | D1 | toluene | Pig1 | A | A | A |
| | 3 | D1 | toluene | Pig2 | A | A | A |
| | 4 | D1 | toluene | Pig3 | A | B | B |
| | 5 | D1 | DMF | Pig1 | A | A | A |
| | 6 | D1 | THF | Pig1 | A | A | A |
| | 7 | D2 | toluene | Pig1 | B | B | B |
| | 8 | D3 | toluene | Pig1 | A | A | A |
| | 9 | D4 | toluene | Pig1 | B | A | A |
| | 10 | D5 | toluene | Pig1 | B | A | A |
| | 11 | D6 | toluene | Pig1 | A | A | A |
| | 12 | D7 | toluene | Pig1 | A | A | A |
| | 13 | D8 | toluene | Pig1 | A | A | A |
| | 14 | D9 | toluene | Pig1 | A | A | B |
| | 15 | D10 | toluene | Pig1 | A | A | A |
| | 16 | D11 | toluene | Pig1 | A | A | A |
| | 17 | D12 | toluene | Pig1 | A | A | A |
| | 18 | D13 | toluene | Pig1 | A | A | A |
| | 19 | D14 | toluene | Pig1 | B | A | A |
| | 20 | D15 | toluene | Pig1 | B | A | A |
| | 21 | D16 | toluene | Pig1 | A | A | A |
| | 22 | D17 | toluene | Pig1 | A | A | A |
| | 23 | D18 | toluene | Pig1 | A | A | A |
| | 24 | D19 | toluene | Pig1 | A | A | A |
| | 25 | D20 | toluene | Pig1 | B | B | C |
| | 26 | D21 | toluene | Pig1 | A | A | C |
| | 27 | D22 | toluene | Pig1 | A | A | B |
| | 28 | D23 | toluene | Pig1 | A | A | A |
| | 29 | D24 | toluene | Pig1 | B | A | A |
| | 30 | D25 | toluene | Pig1 | B | A | A |
| | 31 | D26 | toluene | Pig1 | B | A | B |
| | 32 | D27 | toluene | Pig1 | C | A | C |
| | 33 | D28 | toluene | Pig1 | A | A | A |
| | 34 | D29 | toluene | Pig1 | A | A | A |
| | 35 | D30 | toluene | Pig1 | B | A | A |
| | 36 | D31 | toluene | Pig1 | B | A | B |
| | 37 | D32 | toluene | Pig1 | B | B | B |
| | 38 | D33 | toluene | Pig1 | C | B | C |
| | 39 | D34 | toluene | Pig1 | A | B | B |
| | 40 | D35 | toluene | Pig1 | A | A | A |
| | 41 | D36 | toluene | Pig1 | A | B | B |
| | 42 | D37 | toluene | Pig1 | B | A | B |
| Comparative Examples | 1 | D38 | toluene | Pig1 | D | B | D |
| | 2 | D39 | toluene | Pig1 | A | D | D |
| | 3 | D40 | toluene | Pig1 | B | D | D |
| | 4 | D41 | toluene | Pig1 | A | D | D |
| | 5 | D42 | toluene | Pig1 | D | C | D |

TABLE 7-continued

Evaluation Results of the Dispersants

| | Dispersant | Medium for Evaluation | Coloring Material | Solubility | Adsorbability to Coloring Material | Coloring Material Dispersibility |
|---|---|---|---|---|---|---|
| 6 | D43 | toluene | Pig1 | B | C | D |
| 7 | D44 | toluene | Pig1 | D | B | D |

CB: carbon black
Pig1: C.I. Pigment Red 122
Pig2: C.I. Pigment Blue 15:3
Pig3: C.I. Pigment Yellow 155

As is clear from the results shown in Table 7, any of the Dispersants of Examples was good in the solubility to the medium, and excellent in the adsorbability to the coloring material. Further the Dispersants of Examples exhibited excellent coloring material dispersibility in the organic solvent.

Here, Dispersant (D44) of Comparative Example 7 was colored to yellow and had a strong absorption nearly at a wavelength of 380 nm. By contrast, Dispersants (D1) to (D37) were colored to from pink to red, which were, however, fairly light colors. Further although Dispersants (D1) to (D37) exhibited absorption nearly at a wavelength of 480 to 490 nm, the coloring was in such a degree that the absorption could not be detected unless the concentration of the Dispersants was made to be higher by 5,000 times than that of Dispersant (D44).

(Evaluation of the Coloring Power of the Toners)

Toners in cartridges for a commercially available color laser printer Satera LBP7700C (manufactured by Canon Inc.) were extracted from the cartridges; and after the interiors thereof were cleaned by air blow, each Toner (150 g) was filled therein. Further, the Satera LBP7700C (manufactured by Canon Inc.) was partially remodeled by removing the fixing assembly so as to be able to output unfixed images, and further remodeled so as to operate even on the installation of only a process cartridge of one color. The cartridge was installed on the printer; the amount of Toner to be applied was set so as to become 0.30 mg/cm$^2$; and a solid image of a rectangle of 6.5 cm×14.0 cm was outputted on the center of a transfer material to thereby make an image for evaluation. The transfer medium used was a letter-size HP LASERJET PAPER (manufactured by Hewlett-Packard Development Co., 90.0 g/m$^2$).

By using an external fixing assembly of the LBP7700C, the outputted image for evaluation was fixed at a process speed of 280 mm/sec at 150° C.; and the image density was measured and the coloring power was evaluated. Here, the measurement of the image density was carried out using an "X-Rite color reflection densitometer X-Rite 404A". The relative densities, of five points of top right, top left, center, bottom right and bottom left in a solid image, with respect to a printout image of a white ground portion, whose manuscript density was 0.00, were measured, and the average was taken as an image density. The evaluation criteria were as follows, where C or higher rank was considered to be levels providing the effect of the present invention. The results of each Toner are shown in Table 8.
A: the image density was 1.50 or higher
B: the image density was 1.35 or higher and lower than 1.50
C: the image density was 1.20 or higher and lower than 1.35
D: the image density was lower than 1.20.

TABLE 8

Evaluation Results of the Toners

| Examples Comparative Examples | Toner | Dispersant | Image coloring Power |
|---|---|---|---|
| Example 101 | Toner 1 | D1 | A |
| Example 102 | Toner 2 | D1 | A |
| Example 103 | Toner 3 | D1 | A |
| Example 104 | Toner 4 | D1 | A |
| Example 105 | Toner 5 | D1 | A |
| Example 106 | Toner 6 | D1 | A |
| Example 107 | Toner 7 | D2 | C |
| Example 108 | Toner 8 | D3 | A |
| Example 109 | Toner 9 | D4 | B |
| Example 110 | Toner 10 | D5 | B |
| Example 111 | Toner 11 | D6 | A |
| Example 112 | Toner 12 | D7 | A |
| Example 113 | Toner 13 | D8 | A |
| Example 114 | Toner 14 | D9 | A |
| Example 115 | Toner 15 | D10 | A |
| Example 116 | Toner 16 | D11 | A |
| Example 117 | Toner 17 | D12 | A |
| Example 118 | Toner 18 | D13 | A |
| Example 119 | Toner 19 | D14 | B |
| Example 120 | Toner 20 | D15 | B |
| Example 121 | Toner 21 | D16 | A |
| Example 122 | Toner 22 | D17 | A |
| Example 123 | Toner 23 | D18 | A |
| Example 124 | Toner 24 | D19 | A |
| Example 125 | Toner 25 | D20 | C |
| Example 126 | Toner 26 | D21 | B |
| Example 127 | Toner 27 | D22 | B |
| Example 128 | Toner 28 | D23 | A |
| Example 129 | Toner 29 | D24 | B |
| Example 130 | Toner 30 | D25 | B |
| Example 131 | Toner 31 | D26 | B |
| Example 132 | Toner 32 | D27 | B |
| Example 133 | Toner 33 | D28 | A |
| Example 134 | Toner 34 | D29 | A |
| Example 135 | Toner 35 | D30 | B |
| Example 136 | Toner 36 | D31 | C |
| Example 137 | Toner 37 | D32 | C |
| Example 138 | Toner 38 | D33 | C |
| Example 139 | Toner 39 | D34 | B |
| Example 140 | Toner 40 | D35 | A |
| Example 141 | Toner 41 | D36 | B |
| Example 142 | Toner 42 | D37 | B |
| Comparative Example 101 | Toner 43 | D38 | D |
| Comparative Example 102 | Toner 44 | D39 | D |
| Comparative Example 103 | Toner 45 | D40 | D |
| Comparative Example 104 | Toner 46 | D41 | D |
| Comparative Example 105 | Toner 47 | D42 | C |
| Comparative Example 106 | Toner 48 | D43 | C |
| Comparative Example 107 | Toner 49 | D44 | B |

From the results of Table 8, it became clear that the Toners 1 to 42, which used the Dispersants according to the present invention, were superior in coloring power to the Toners 43 to 48, which used the Dispersants of Comparative Examples.

On the other hand, although Toner 49, which used Dispersant D44, had a good coloring power of B rank, Toner 49 exhibited a shift observed in the hue angle as compared with the case of Toner 4, which used Dispersant D1. Specifically, images different in density of Toner 4 and Toner 49 were prepared; and respective a*, b* and c* ($=\sqrt{(a*^2+b*^2)}$)) were measured by a SpectroScan Transmission (manufactured by GretagMacbeth Co.), and approximate curves were obtained. Comparing values of a* and b* when c* of the both became 75, the b* value of Toner 49 varied to a largely plus direction (shifted to the yellowish side) as compared with that of Toner 4.

The dispersant according to the present invention is superior to conventional dispersants in the solubility to the solvents, the adsorption power to the coloring materials, and the dispersibility of the coloring materials, and is a dispersant broadly applicable to coloring materials different in kind. Further the compound according to the present invention is a compound useful for preparation of the dispersant. The dispersant according to the present invention is utilized for coating materials, power coating materials, toners and the like, and exhibits excellent coloring power.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-176818, filed Sep. 1, 2014, which is hereby incorporated by reference herein in its entirety.

What is claimed is:

1. A compound represented by formula (2) or a tautomer thereof:

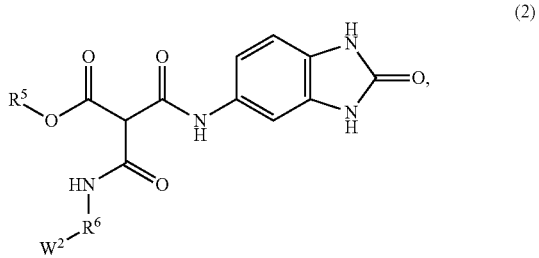

wherein:
$R^5$ represents an alkyl group having 2 to 12 carbon atoms or a benzyl group;
$R^6$ represents an alkylene group having 2 to 4 carbon atoms; and
$W^2$ represents an amino group, an acryloyloxy group, a methacryloyloxy group, an acryloylamino group, or a methacryloylamino group.

2. The compound according to claim 1, wherein $W^2$ in the formula (2) is an acryloyloxy group or a methacryloyloxy group.

3. The compound according to claim 1, wherein $R^5$ in the formula (2) is an alkyl group having 2 to 8 carbon atoms.

4. A dispersant comprising a structure in which a structure represented by formula (3) or a tautomer thereof is bonded with a polymer moiety:

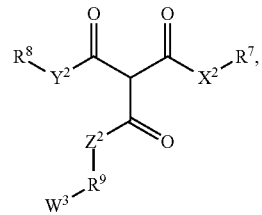

wherein:
each of $X^2$, $Y^2$, and $Z^2$ is, independently, —O—, a methylene group, or —NR$^{10}$—;
$R^{10}$ represents hydrogen or a straight-chain or branched-chain alkyl group having 1 to 4 carbon atoms;
$R^7$ represents an unsubstituted or substituted phenyl group, a polycyclic aromatic group, or a heterocyclic group;
$R^8$ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond, or an amide bond;
$R^9$ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond, or an amide bond;
$W^3$ represents a linking moiety to the polymer moiety;
a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group, or a ureido group;
the polycyclic aromatic group is a group derived from naphthalene, anthracene, phenanthrene, or anthraquinone by removing one hydrogen atom therefrom; and
the heterocyclic group is a group derived from imidazole, oxazole, thiazole, pyridine, indole, benzimidazole, benzimidazolinone, or phthalimide by removing one hydrogen atom therefrom.

5. The dispersant according to claim 4, wherein the structure represented by the formula (3) or the tautomer thereof is a structure represented by formula (4) or a tautomer thereof:

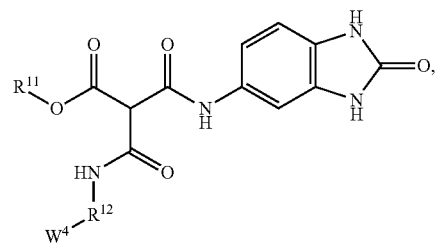

wherein:
R¹¹ represents an alkyl group having 2 to 12 carbon atoms or a benzyl group;
R¹² represents an alkylene group having 2 to 4 carbon atoms; and
W⁴ represents a linking moiety to a polymer moiety, and the linking moiety is an ester bond or an amide bond.

6. The dispersant according to claim 5, wherein the R¹¹ is an alkyl group having 2 to 8 carbon atoms.

7. The dispersant according to claim 4, wherein the polymer moiety has a vinylic copolymer structure or a polyester structure.

8. The dispersant according to claim 7, wherein the vinylic copolymer structure has at least one of a unit B originated from a compound B being an aromatic vinyl monomer and a unit C originated from a compound C being an acrylic acid-based monomer or a methacrylic acid-based monomer.

9. The dispersant according to claim 8, wherein the dispersant satisfies formula (5):

$$0.01 \leq a/(b+c) \leq 2.00 \quad (5),$$

wherein:
a represents a content (parts by mole) of the structure represented by the formula (3);
b represents a content (parts by mole) of the unit B in terms of a molecular weight of the compound B; and
c represents a content (parts by mole) of the unit C in terms of a molecular weight of the compound C.

10. A toner comprising a toner particle comprising a binder resin, a coloring material, and a dispersant,
wherein the dispersant has a structure in which a structure represented by formula (3) or a tautomer thereof is bonded with a polymer moiety:

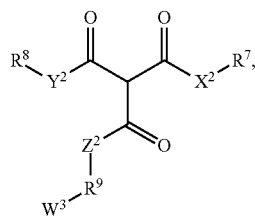
(3)

wherein:
each of X², Y², and Z² is, independently, —O—, a methylene group, or —NR¹⁰—;

R¹⁰ represents hydrogen or a straight-chain or branched-chain alkyl group having 1 to 4 carbon atoms;

R⁷ represents an unsubstituted or substituted phenyl group, a polycyclic aromatic group, or a heterocyclic group;

R⁸ represents a hydrogen atom, an unsubstituted or substituted phenyl group, an aralkyl group, a straight-chain, branched-chain or cyclic alkyl group having 1 to 18 carbon atoms, or a monovalent group derived from an alkyl group having 1 to 18 carbon atoms by replacing a methylene group thereof by an ether bond, an ester bond, or an amide bond;

R⁹ represents an unsubstituted or substituted phenylene group, a straight-chain, branched-chain or cyclic alkylene group having 1 to 18 carbon atoms, or a divalent group derived from an alkylene group having 1 to 18 carbon atoms by replacing a methylene group in the main chain thereof by an ether bond, an ester bond, or an amide bond;

W³ represents a linking moiety to the polymer moiety;

a substituent of the substituted phenyl group and a substituent of the substituted phenylene group are each a methyl group, a methoxy group, a hydroxy group, a nitro group, a chloro group, a carboxy group, an amino group, a dimethylamino group, a carboxylic acid amide group, or a ureido group;

the polycyclic aromatic group is a group derived from naphthalene, anthracene, phenanthrene, or anthraquinone by removing one hydrogen atom therefrom; and the heterocyclic group is a group derived from imidazole, oxazole, thiazole, pyridine, indole, benzimidazole, benzimidazolinone, or phthalimide by removing one hydrogen atom therefrom.

* * * * *